United States Patent
Mattei et al.

(10) Patent No.: US 6,703,397 B2
(45) Date of Patent: Mar. 9, 2004

(54) PYRIMIDINYL METHYL INDOLE DERIVATIVES WITH ANTIBACTERIAL ACTIVITY

(75) Inventors: Patrizio Mattei, Riehen (CH); Philippe Pflieger, Schwoben (FR)

(73) Assignee: Basilea Pharmaceutica AG (CH)

( * ) Notice: Subject to any disclaimer, the term of this patent is extended or adjusted under 35 U.S.C. 154(b) by 0 days.

(21) Appl. No.: 10/258,687

(22) PCT Filed: Apr. 20, 2001

(86) PCT No.: PCT/EP01/04542

§ 371 (c)(1),
(2), (4) Date: Oct. 25, 2002

(87) PCT Pub. No.: WO01/83474

PCT Pub. Date: Nov. 8, 2001

(65) Prior Publication Data

US 2003/0119857 A1 Jun. 26, 2003

(30) Foreign Application Priority Data

Apr. 27, 2000 (EP) .............................................. 00108944

(51) Int. Cl.$^7$ .................... C07D 403/06; C07D 405/14; A61K 31/505
(52) U.S. Cl. ................. 514/275; 514/228.2; 514/235.2; 514/235.8; 544/62; 544/122; 544/324
(58) Field of Search .......................... 544/324, 62, 122; 514/275, 235.2, 235.8, 228.2

(56) References Cited

U.S. PATENT DOCUMENTS

| | | | |
|---|---|---|---|
| 3,316,267 A | 4/1967 | Shen et al. | 260/250 |
| 4,590,271 A | 5/1986 | Daluge et al. | 544/324 |
| 5,721,242 A | 2/1998 | Kompis et al. | 514/272 |

OTHER PUBLICATIONS

Nau et al., PubMed Abstract (Clin. Pharmacokinet. 35(3):223–46), 1998.*

Then et al., Advances in Experimental Medicine and Biology, vol. 338, pp. 533–536 (1993).

* cited by examiner

*Primary Examiner*—Deepak Rao
(74) *Attorney, Agent, or Firm*—Gibbons, Del Deo, Dolan, Griffinger & Vecchione

(57) ABSTRACT

This invention relates to indole derivatives of the general formula (I) wherein $R^1$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl or phenylalkyl; $R^2$ is hydrogen, halogen, alkyl, alkanoyl, phenyl, phenylalkyl or heterocyclylalkyl; $R^3$ is hydrogen, alkyl; and $R^4$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl, or phenylalkyl; and pharmaceutically acceptable acid addition salts of these compounds, there use as therapeutically active substances; medicaments based on these substances, optionally in combination with sulphonamides, and their production; the use of these substances as medicaments and for the production of antibacterially-active medicaments; as well as the manufacture of the compounds of formula (I) and their pharmaceutically acceptable acid addition salts and intermediates for their manufacture.

(I)

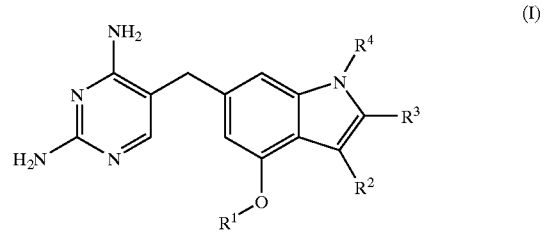

14 Claims, No Drawings

PYRIMIDINYL METHYL INDOLE DERIVATIVES WITH ANTIBACTERIAL ACTIVITY

This application is a 371 of PCT/EP01/04542 filed Apr. 20, 2001.

This invention relates to indole derivatives of the general formula:

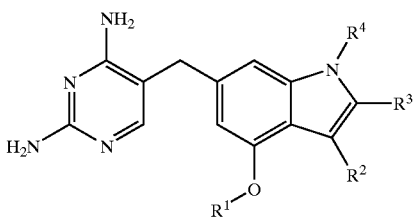

wherein
- $R^1$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl or phenylalkyl;
- $R^2$ is hydrogen, halogen, alkyl, alkanoyl, phenyl, phenylalkyl or heterocyclylalkyl;
- $R^3$ is hydrogen, alkyl; and
- $R^4$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl, or phenylalkyl;

and pharmaceutically acceptable acid addition salts of these compounds.

The above compounds are novel and possess valuable antibiotic properties. They can be used in the control and prevention of infectious diseases. In particular, they exhibit a pronounced antibacterial activity, including multi-resistant gram-positive strains, such as *Streptococcus pneumoniae* and *Staphylococcus aureus*. These compounds can also be administered in combination with known antibacterially active substances and then exhibit a synergistic effect. Typical combination partners are, e.g., sulfonamides, which can be admixed with the compounds of formula I or their salts in various ratios.

Objects of the present invention are compounds of formula I and their pharmaceutically acceptable salts per se and their use as therapeutically active substances; medicaments based on these substances, optionally in combination with sulfonamides, and their production; the use of these substances as medicaments and for the production of antibacterially active medicaments; as well as the manufacture of the compounds of formula I and their pharmaceutically acceptable salts and intermediates for their manufacture.

The residues named above are defined below. In combined residues such as cycloalkylalkyl etc. the exemplification is to be understood accordingly.

The term "Halogen" denotes fluorine, chlorine, bromine or iodine, preferably fluorine, chlorine or bromine.

The term "Alkyl" denotes a straight chained or branched group which carries up to and including 6, preferably 4 carbon atoms, if not otherwise specified. Such groups are, e.g., methyl, ethyl, n-propyl, isopropyl, isobutyl, sec-butyl or t-butyl.

"Alkenyl" and "alkynyl" denote unsaturated straight chain or branched hydrocarbon groups which carry up to and including 6, preferably 4 carbon atoms, having at least one double or one triple bond, respectively, e.g., vinyl, 2-propenyl, 1,3-butadienyl, isopropenyl, 1-propynyl, 2-propynyl, 1-butynyl, 3-butynyl.

"Cycloalkyl" denotes a cyclic hydrocarbon group which carries 3 to 6 carbon atoms, e.g., cyclopropyl, cyclobutyl, cyclopentyl, cyclohexyl.

"Cycloalkylalkyl" denotes the combination of cycloalkyl and alkyl as defined above, e.g., cyclopropylmethyl, 2-cyclopropylethyl, cyclopentylmethyl.

"Alkanoyl" denotes the formyl group or an alkyl-CO-group, where "alkyl" is as defined above.

"Heterocyclyl" refers to heterocyclic, saturated 3 to 6 membered rings containing one or two heteroatoms selected from nitrogen, oxygen and sulfur, e.g., aziridinyl, oxiranyl, thiiranyl, azetidinyl, oxetanyl, thietanyl, pyrrolidinyl, tetrahydrofuryl, tetrahydrothienyl, piperidyl, tetrahydropyranyl, tetrahydrothiopyranyl, morpholinyl, thiomorpholinyl, piperazinyl, dioxolanyl, imidazolidinyl, oxazolidinyl, isoxazolidinyl, thiazolidinyl, pyrazolidinyl, or 1,4-dioxo-8-aza-spiro[4.5]decan-8-yl etc., the heterocyclic group may be substituted by one or more substituents such as alkyl, alkoxy, halogen, alkanoyl or phenyl. "Phenyl" refers to unsubstituted phenyl and phenyl substituted by one or more substituents such as alkyl, alkoxy, halogen, alkanoyl or phenyl.

Preferred compounds of formula I are the compounds wherein $R^1$ is alkylsulfonyl, cycloalkylsulfonyl, or cycloalkylalkylsulfonyl, particularly isopropylsulfonyl, isobutyl-sulfonyl, sec-butylsulfonyl, cyclopropylsulfonyl or cyclopropylmethylsulfonyl. Preferred meanings for $R^2$ are hydrogen or alkyl, particularly methyl. Preferred meanings for $R^3$ are hydrogen or methyl. Preferred meanings for $R^4$ is alkyl, particularly ethyl.

Preferred compounds of formula I are:
- cyclopropyl-methanesulfonic acid 6-(2,4-diamino-pyrimidin-5-ylmethyl)-1-ethyl-1H-indol-4-yl ester;
- 2-methyl-propane-1-sulfonic acid 6-(2,4-diamino-pyrimidin-5-ylmethyl)-1-ethyl-1H-indol-4-yl ester;
- rac-butane-2-sulfonic acid 6-(2,4-diamino-pyrimidin-5-ylmethyl)-1-ethyl-1H-indol-4-yl ester;
- cyclopropyl-methanesulfonic acid 6-(2,4-diamino-pyrimidin-5-ylmethyl)-1-ethyl-3-methyl-1H-indol-4-yl ester; and
- rac-butane-2-sulfonic acid 6-(2,4-diamino-pyrimidin-5-ylmethyl)-1-ethyl-2-methyl-1H-indol-4-yl ester;

and pharmaceutically acceptable acid addition salts of these compounds.

The compounds of formula I form pharmaceutically acceptable acid addition salts with organic and inorganic acids. Examples of acid addition salts of compounds of formula I are salts with mineral acids, for example hydrohalic acids such as hydrochloric acid, hydrobromic acid and hydriodic acid, sulphuric acid, nitric acid, phosphoric acid and the like, salts with organic sulfonic acids, for example with alkyl- and arylsulfonic acids such as methanesulfonic acid, p-toluene sulfonic acid, benzenesulfonic acid and the like as well as salts with organic carboxylic acids, for example with acetic acid, tartaric acid, maleic acid, citric acid, benzoic acid, salicylic acid, ascorbic acid and the like.

The compounds of formula I and their pharmaceutically acceptable salts can be manufactured in accordance with the invention by i) reacting a compound of the general formula:

II in which $R^1$–$R^4$ have the above significance, and X represents a leaving group, with guanidine or a salt thereof, or ii) introducing at least one of the groups $R^1$, $R^2$ and $R^4$ in a compound of the general formula:

III in which $R^3$ is as above and $R^{1A}$, $R^{2A}$ and $R^{4A}$ are as $R^1$, $R^2$ and $R^4$ but at least one, thereof is hydrogen, or iii) converting a compound of formula I into a pharmaceutically acceptable salt.

The cyclization of the starting materials II (where the =CHX group can be either in (E)- or (Z)-configuration) with guanidine or a salt thereof in accordance with variant i) of the process in accordance with the invention is preferably carried out in an inert organic solvent, preferably in a lower alkanol, e.g., ethanol, or in dimethyl sulfoxide, tetrahydrofuran or dioxane, and at about 50 to 100° C. The guanidine is preferably used as a salt, e.g.) as the hydrochloride, in which case the reaction is preferably carried out in the presence of a base, e.g., potassium t-butylate. The leaving group X is preferably bromine, iodine, methylsulfonyloxy, trifluoromethylsulfonyloxy, phenylsulfonyloxy or p-tolylsulfonyloxy.

Variant ii) of the process in accordance of the invention contains several alternatives. A phenyl or heterocyclyl group $R^2$ can be introduced by reacting a compound of the general formula:

IIIa with a compound of the general formula:

$R^{21}$—Y                                   IV in which
$R^1$, $R^3$ and $R^4$ have the above significance,
$R^{21}$ is phenyl (which may be substituted)

one of the symbols X and Y represent a leaving group and the other is a group which is eliminated with this leaving group.

In this reaction groups X and Y can be:
X=bromine, iodine, methylsulfonyloxy, trifluoromethylsulfonyloxy, phenyl-sulfonyloxy or p-tolylsulfonyloxy; and
Y=$(OH)_2B$—.

This reaction with a boronic acid derivative IV, also known as a "Suzuki coupling", is preferably effected in an inert organic solvent such as, e.g., dioxane, tetrahydrofuran or dimethyl sulfoxide at a temperature between about 20° C. and the boiling point of the reaction mixture. Preferably, a base such as an alkali metal carbonate, e.g., potassium carbonate, is preferably added as well as a catalyst, preferably a palladium complex such as tetrakistriphenylphosphine-palladium.

A compound IV with Y=—Sn(lower-alkyl)$_3$, e.g., —Sn(CH$_3$)$_3$ or —Sn(n-butyl)$_3$ ("Stille reaction"); —MgHal ("Grignard coupling"); or —ZnHal and Hal=chlorine, bromine or iodine ("Negishi coupling") can be used in the above reaction as the reaction partner of formula IV. No base is used in this reaction, although the catalyst described above is preferably used. It can also be advantageous to add an inert salt, especially lithium chloride.

The aforementioned reaction can also be carried out with interchanged substituents X and Y, e.g., with X=—Sn(CH$_3$)$_3$, —MgHal or —ZnHal and Y=bromine, iodine, methylsulfonyloxy, trifluoromethylsulfonyloxy, phenylsulfonyloxy, p-tolylsulfonyloxy. The reaction conditions are essentially the same.

Further methods for introducing $R^2$ are halogenation, alkanoylation, amino-methylation and conversion of the aminomethyl group to methyl, all according to methods disclosed below as process steps (p), (r), (s) and (t).

Groups $R^1$ and $R^4$ can be introduced by reacting a compound of the general formulas:

IIIb

IIIc with a compound of the general formula:

$R^1Z$ or $R^4Z$, respectively, in which $R^1$–$R^4$ are as defined above and Z is a leaving group.

The leaving group Z, in the case of an alkylation reaction, is preferably bromine, iodine, methylsulfonyloxy, trifluoromethylsulfonyloxy, phenylsulfonyloxy or p-tolylsulfonyloxy. For a sulfonylation reaction Z is preferably chlorine. The reaction is preferably carried out in a polar aprotic solvent such as N,N-dimethylformamide and in the presence of a base, e.g., potassium tert-butoxide, at a temperature of about −20° C. to 20° C.

The manufacture of the pharmaceutically acceptable acid addition salts of the compounds of formula I in accordance with variant iii) can be effected in a manner known per se, e.g., by reacting a compound of formula I with an organic or inorganic acid in an organic solvent such as ethanol, methanol or acetone. The temperature at which the salt formation is carried out is not critical. It generally lies at room temperature, but can also be lower or higher, for example in the range of 0° C. to +50° C.

Various possibilities for synthesising the compounds of the general formula I are outlined in the following reaction schemes 1–6.

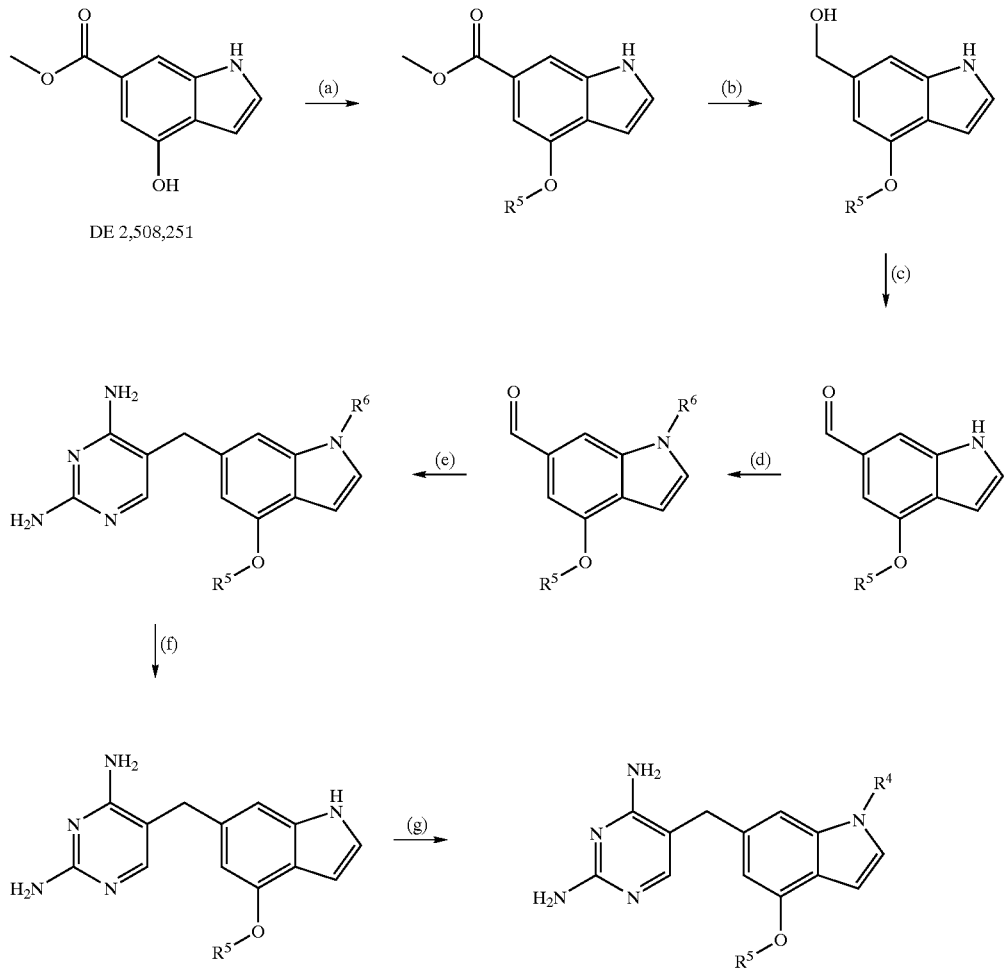

Scheme 1

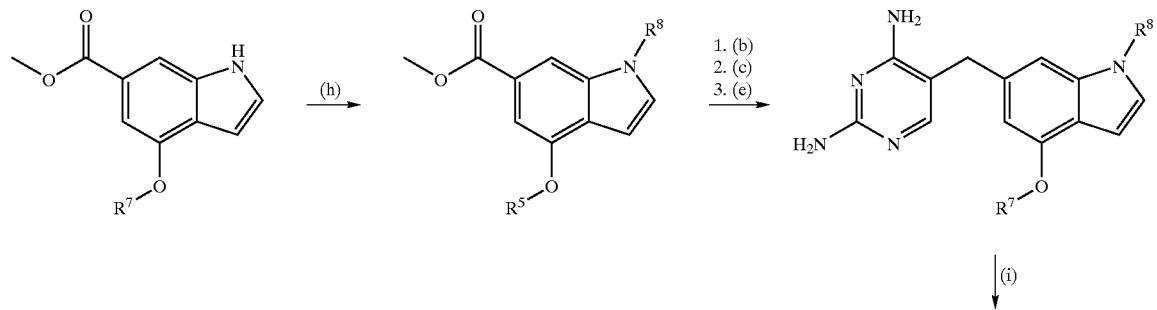

Scheme 2

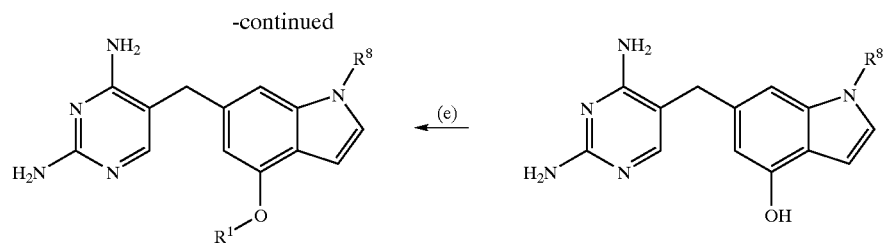
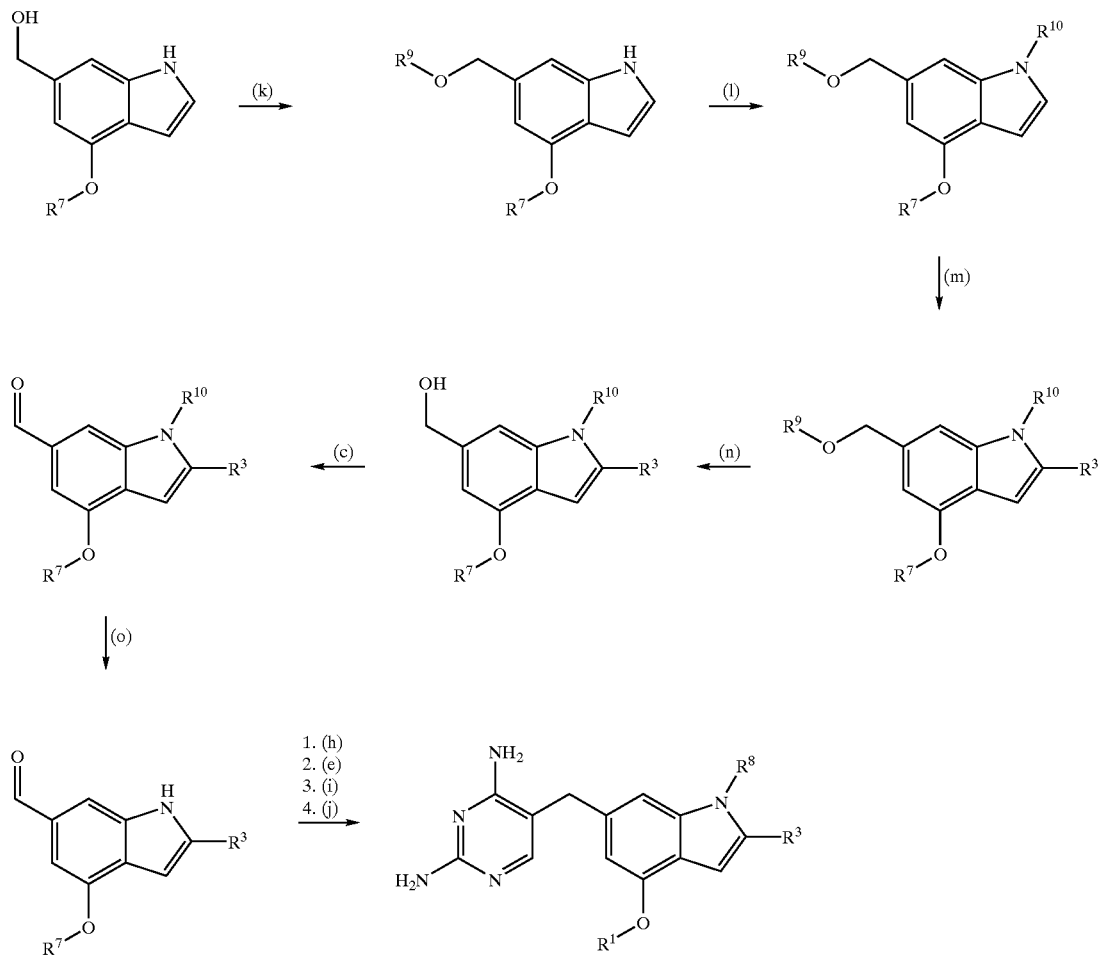
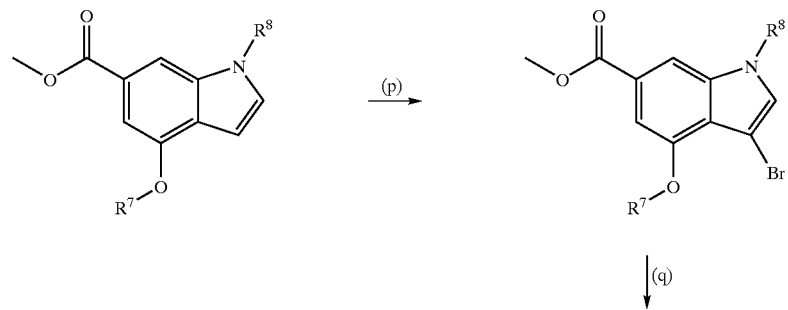

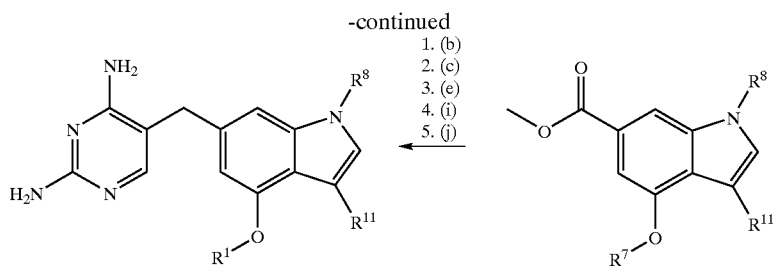

Scheme 5

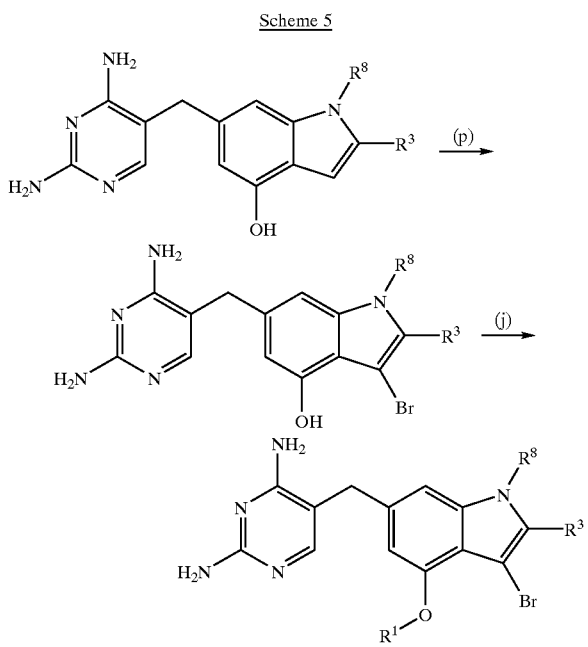

In Schemata 1–6 the symbols are defined as follows:

$R^1$, $R^2$, $R^3$, and $R^4$ are as defined above;

$R^5$ is alkyl, alkenyl, alkynyl, cycloalkyl, cycloalkylalkyl, heterocyclylalkyl or phenylalkyl;

$R^6$ represents a suitable protecting group, especially 2-trimethylsilanyl-ethoxymethyl;

$R^7$ represents a suitable protecting group, especially 2-trimethylsilanyl-ethoxymethyl, benzyl or a derivative thereof;

$R^8$ is alkyl, alkenyl, alkynyl, cycloalkyl, heterocyclylalkyl or phenylalkyl;

$R^9$ represents a suitable protecting group, especially tetrahydropyran-2-yl or a derivative thereof;

$R^{10}$ represents a suitable protecting group, especially alkylsulfonyl, phenylsulfonyl, or a derivative thereof;

$R^{11}$ is aryl, heterocyclyl;

$R^{12}$ is hydrogen, alkyl;

$R^{13}$ is dialkylamino including nitrogen-containing heterocycles, which are attached through a nitrogen atom, especially morpholin-4-yl and thiomorpholin-4-yl.

The reaction steps (a)–(t) are preferably carried out as follows:

(a) Alkylation of the hydroxyl of a 1H-indol-4-ol. This reaction is carried out with a compound of the general

Scheme 6

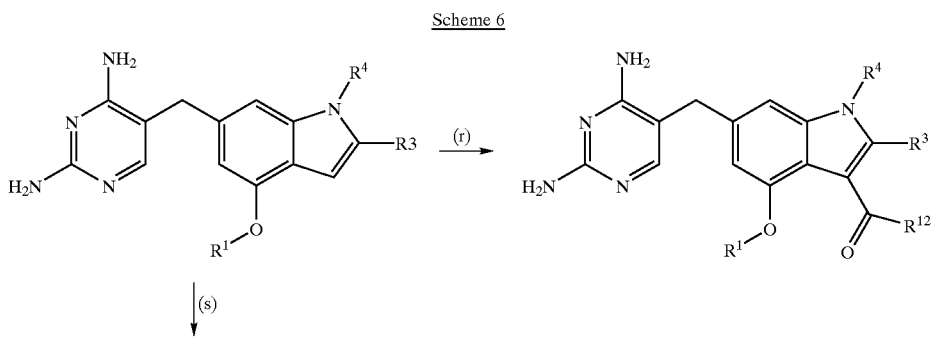

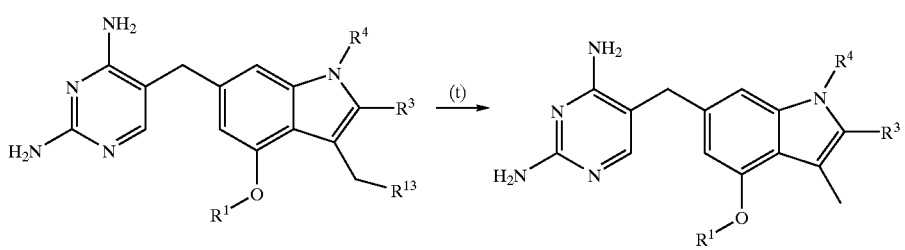

formula $R^5$—X, where X is a leaving group, preferably Br, in a polar aprotic solvent such as N,N-dimethylformamide and in the presence of a base, preferably potassium tert-butylate, at about 0–30° C.

(b) Reduction of the ester function of a methyl 1H-indole 6-carboxylate to the corresponding alcohol. This reaction is carried out using an excess of an aluminum hydride, especially diisobutylaluminumhyride, in a solvent such as tetrahydrofuran, at about 0–20° C.

(c) Oxidation of the alcohol group of a [1H-indol-6-yl]-methanol to the corresponding aldehyde. This reaction is carried out using an excess of manganese dioxide in a solvent such as dichloromethane, at temperatures between 0° C. and the boiling point of the solvent.

(d) Protection of the 1H-indole nitrogen. This reaction is carried out with a compound of the formula $R^6$—X, where X is a leaving group, e. g., Cl, in the presence of base, preferably potassium tert-butylate, in a polar solvent such as N,N-dimethylformamide, at about 0–30° C.

(e) Transformation of a 1H-indole-6-carbaldehyde to a 5-(1H-indol-6-ylmethyl)-2,4,diaminopyrimidine. This two-step sequence is performed by (e1) base-catalyzed condensation of the 1H-indole-6-carbaldehyde with 3-anilinopropionitrile and, (e2) subsequent treatment of the 1-anilino-2-(1H-indol-6-ylmethyl)acrylonitrile formed with guanidine, applying a method described in patent DE2443682.

(f) Cleavage of the 1H-indole nitrogen protective group, $R^6$. This reaction is preferably carried out with tetrabutylammonium fluoride in tetrahydrofuran, in the presence of ethylenediamine and molecular sieves, at temperatures between 20° C. and the boiling point of the solvent.

(g) Functionalization of the 1H-indole nitrogen. This reaction is carried out with a compound of the formula $R^8$—X (in the case of an alkylation reaction) or $R^{14}$—Cl (in the case of a sulfonation reaction), in a polar aprotic solvent such as N,N-dimethylformamide and in the presence of a base, e. g., potassium tert-butoxide, at temperatures between –20° C. and 20° C. X is a leaving group, preferably Br, and $R^{14}$ is alkylsulfonyl, cycloalkylsulfonyl, cycloalkylalkylsulfonyl, dialkylsulfamoyl, or N-cycloalkyl-N-alkylsulfamoyl.

(h) Functionalization of the 1H-indole nitrogen. This reaction is carried out with a compound of the formula or $R^8$—X, in a polar aprotic solvent such as N,N-dimethylformamide and in the presence of a base, e. g., potassium tert-butoxide, at temperatures between –20° C. and 20° C. X is a leaving group, preferably Br.

(i) Cleavage of the phenol protecting group, $R^7$. This reaction is carried out,
   (i1) in the case $R^7$=2-trimethylsilanyl-ethoxymethyl, either by tetrabutylammonium fluoride in tetrahydrofuran, or by a strong acid, such as sulfuric acid, in a lower alcohol, at temperatures between 0° C. and the boiling point of the solvent;
   (i2) in the case $R^7$=benzyl, by catalytic hydrogenation using hydrogen and palladium on activated charcoal, in a lower alcohol or a low alkanecarboxylic acid, at about 0–50° C., preferably at room temperature.

(j) Functionalization of the hydroxyl of a 1H-indol-4-ol. This reaction is carried with a compound of the formula or $R^8$—X (in the case of an alkylation reaction) or $R^{14}$—Cl (in the case of a sulfonation reaction), in a polar aprotic solvent such as N,N-dimethyl-formamide and in the presence of a base, e. g., potassium tert-butoxide, at temperatures between –20° C. and 20° C. X is a leaving group, preferably Br, and $R^{14}$ is as defined above.

(k) Protection of the hydroxyl of a 1H-indol-6-ylmethanol. This reaction is carried out using 3,4-dihydro-2H-pyran and a catalytic amount of pyridinium toluene-4-sulfonate, in a solvent such as dichloromethane, at about room temperature.

(l) Protection of the nitrogen of a 1H-indole. This reaction is carried out with a suitable sulfonyl chloride, $R^{10}$—Cl, preferably benzenesulfonyl chloride, at about 0–50° C., in a two-phase mixture of aqueous alkali hydroxide and dichloromethane, in the presence of a phase-transfer catalyst such as tetrabutylammonium hydrogensulfate.

(m) Alkylation of a N(1)-protected 1H-indole at C.(2). This reaction is carried out by deprotonation with tert-butyllithium in a solvent such as tetrahydrofuran and subsequent treatment of the 2-lithioindole formed with a compound of the formula $R^3$—X, where X is a leaving group, e.g., I.

(n) Cleavage of the hydroxyl protective group, $R^9$. This reaction is carried out in a lower alcohol such as ethanol using a catalytic amount of pyridinium toluene-4-sulfonate, at temperatures between about 30° C. and the boiling point of the solvent.

(o) Cleavage of the nitrogen protecting group of a 1H-indole, $R^{10}$. This reaction is carried out by hydrolysis in aqueous base, at temperatures between 20° C. and the boiling point of the solvent, where water miscible organic solvents such as lower alcohols and/or tetrahydrofuran are added for increased solubility.

(p) Bromination of a 1H-indole at C(3). This reaction is preferably carried out using elemental bromine in a solvent such as N,N-dimethylformamide, at about 0–40° C.

(q) Coupling reaction of a 3-bromo-1H-indole with a boronic acid, $R^{11}$—B(OH)$_2$ (Suzuki coupling). This reaction is carried out preferably in an inert solvent such as 1,2-dimethoxyethane, at temperatures between about 20° C. and the boiling point of the solvent. The reaction also requires a base, preferably an alkali carbonate, such as potassium carbonate, and a catalytic amount of a palladium complex such as tetrakis(triphenylphosphine) palladium(0).

(r) Alkanoylation of a 1H-indole at C(3). This reaction is preferably carried out by the Vilsmeier method, using an N,N-disubstituted alkanamide, e.g., N,N-dimethylformamide, and phosphorus oxychloride as reagents and the same N,N-dialkylalkanamide as the solvent at a temperature of about 0–80° C.

(s) Aminomethylation of a 1H-indole at C(3). This reaction is carried out by the Mannich method, using a tertiary amine, e. g., morpholine, and formaldehyde as reagents, in a mixture of water and a low alkanecarboxylic acid, e. g., acetic acid, at about 0–80° C.

(t) Conversion of a 3-(aminomethyl)-1H-indole to a 3-methyl-1H-indole. This reaction is carried out by catalytic hydrogenation using hydrogen and palladium on activated charcoal, in a lower alcohol, at about 0–50° C., preferably at room temperature.

As mentioned earlier, the compounds of formula I and their pharmaceutically acceptable salts possess valuable antibacterial properties. They are active against a large number of pathogenic microorganisms such as, e.g., *Staphylococcus aureus, Streptococcus pneumoniae* etc. by virtue of their action in inhibiting bacterial dihydrofolate reductase (DHFR).

The inhibition of the enzyme was taken as a measurement for the antibacterial activity. It is determined using the method of Baccanari and Joyner (Biochemistry 20,1710 (1981)); see also P. G. Hartman et al., FEB. 242, 157–160 (1988).

The IC$_{50}$ values (concentration at which the enzyme is inhibited to 50%) are determined graphically.

The following Tables 1 and 2 contain inhibitory concentrations determined in the above test for representative members of the class of compound defined by formula I. The following microorganisms were tested:

Col. 1: MIC Spn ATCC 49619; μg/ml (*Streptococcus pneumoniae* ATCC 49619, trimethoprim- and penicillin-susceptible, reference strain, obtained from American Type Culture Collection).

Col. 2: MIC Spn1/1; μg/ml (*Streptococcus pneumoniae* 1/1, Trimethoprim- and Penicillin-resistant, Serotype 6; clinical isolate, stored at −80° C.). Lit.: H. Locher et al., Can. J. Infect. Dis. 6: Suppl. C, p 469C.

Col. 3: DHFR Spn1/1; μM—the IC$_{50}$-values in μM against the purified DHFR of the above strain Spn1/1; of *Streptococcus pneumoniae*.

TABLE 1

Activities of the preferred compounds.

| Example No. | Spn 49619 MIC [μg/ml] | Spn 1/1 MIC [μg/ml] | Spn 1/1 IC50 [μmol/l] |
|---|---|---|---|
| Trimethoprim | 4 | >32 | 3 |
| Epiroprim | 0.125 | 4 | 0.19 |
| 8b | ≦0.015 | 1 | 0.0015 |
| 8c | ≦0.015 | 2 | 0.0015 |
| 8d | 0.03 | 1 | 0.0018 |
| 12b | ≦0.015 | 4 | 0.0037 |
| 15c | 0.03 | 2 | 0.0087 |

TABLE 2

| Example No. | Spn 49619 MIC [μg/ml] | Spn 1/1 MIC [μg/ml] | Spn 1/1 IC50 [μmol/l] |
|---|---|---|---|
| Trimethoprim | 4 | >32 | 3 |
| Epiroprim | 0.125 | 4 | 0.19 |
| 2a | 0.5 | >8 | 0.11 |
| 2b | 0.5 | 8 | 0.15 |
| 2c | 2 | >8 | 0.46 |
| 2d | 0.5 | >8 | 0.33 |
| 2e | 0.06 | 4 | 0.11 |
| 3 | 0.125 | 4 | 0.024 |
| 5a | 0.25 | 4 | 0.11 |
| 5b | 0.5 | >8 | 0.17 |
| 5c | 0.25 | 4 | 0.084 |
| 5d | 0.125 | 4 | 0.036 |
| 5e | 0.125 | 8 | 0.013 |
| 7a | 0.125 | 4 | 0.021 |
| 7b | 0.5 | 8 | 0.41 |
| 7c | 0.25 | 4 | 0.14 |
| 7d | 0.125 | 8 | 0.071 |
| 7e | 1 | 8 | 0.21 |
| 7f | 0.5 | 2 | 0.041 |
| 7g | 0.5 | 2 | 0.029 |
| 7h | 1 | 4 | 0.015 |
| 7i | 0.5 | 8 | 0.013 |
| 8a | 0.03 | 1 | 0.028 |
| 9 | 0.03 | 2 | 0.029 |
| 10a | 0.25 | 8 | 0.18 |
| 10b | 0.5 | 8 | 0.11 |
| 10c | 1 | 4 | 0.16 |
| 10d | 1 | 8 | 0.25 |
| 10e | 0.125 | 4 | 0.0048 |
| 11 | 0.25 | >8 | 0.093 |
| 12a | 0.125 | 4 | 0.015 |
| 13 | 0.125 | 4 | 0.042 |
| 15a | 0.25 | 8 | 0.056 |
| 15b | 0.5 | 8 | 0.02 |
| 17a | 0.5 | 8 | 0.0063 |
| 17b | 0.5 | 8 | 0.0043 |

The products in accordance with the invention can be used as medicaments, e.g., in the form of pharmaceutical preparations for enteral or parenteral administration. The products in accordance with the invention can be administered, for example, perorally, e.g., in the form of tablets, coated tablets, dragées, hard and soft gelatine capsules, solutions, emulsions or suspensions, rectally, e.g., in the form of suppositories, or parenterally, e.g., in the form of injection solutions. The invention thus also relates to a method of prophylaxis and/or therapeutic treatment of infectious diseases which comprises administering a compound of formula I or pharmaceutically acceptable acid additional salt thereof alone or in combination with a sulfonamide.

The production of the pharmaceutical preparations can be effected in a manner which will be familiar to any person skilled in the art by bringing the substances in accordance with the invention, if desired in combination with other therapeutically valuable substances, into a galenical administration form together with suitable, non-toxic, inert, therapeutically compatible solid or liquid carrier materials and, if desired, the usual pharmaceutical adjuvants.

Not only inorganic carrier materials, but also organic carrier materials are suitable as such carrier materials. Thus, lactose, corn starch or derivatives thereof, talc, stearic acid or its salts can be used, for example, as carrier materials for tablets, coated tablets, dragées and hard gelatine capsules. Suitable carriers for soft gelatine capsules are, for example, vegetable oils, waxes, fats and semi-solid and liquid polyols (depending on the nature of the active substance no carriers are, however, required in the case of soft gelatine capsules). Suitable carrier materials for the production of solutions and syrups are, for example, water, polyols, sucrose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

The usual preservatives, solubilizers, stabilizers, wetting agents, emulsifiers, sweeteners, flavorants, salts for varying the osmotic pressure, buffers, coating agents and antioxidants come into consideration as pharmaceutical adjuvants.

For parenteral administration the compounds of formula I and, respectively their salts are preferably provided as lyophilizates or dry powders for dilution with conventional carriers such as water or isotonic saline.

As already mentioned, the compounds of formula I and their salts have antibacterial activity. They inhibit bacterial dihydrofolate reductase and potentiate the antibacterial activity of sulfonamides such as, e.g., sulfisoxazole, sulfadimethoxine, sulfamethoxazole, 4-sulfanilamido-5,6-dimethoxy-pyrimidine, 2-sulfanilamido-4,5-dimethyl-pyrimidine or sulfaquinoxaline, sulfadiazine, sulfamonomethoxine, 2-sulfanilamido-4,5-dimethyl-isoxazole and other inhibitors of enzymes which are involved in folic acid biosynthesis, such as, e.g., pteridine derivatives.

Oral, rectal and parenteral administration come into consideration for the treatment of hosts, especially warm-blooded hosts, e.g., in human medicine, with the compounds of formula I or combinations thereof with sulfonamides. A daily dosage of about 0.2 g to about 2 g of a compound of formula I in accordance with the invention comes into consideration for adults. When administered in combination with antibacterial sulfon-amides the ratio of compound I to sulfonamide can vary within a wide range; it amounts to, e.g., between 1:40 (parts by weight) and 1:1 (parts by weight); 1:10 to 1:1 are preferred ratios. Thus, e.g., a tablet can contain 80 mg of a compound I in accordance with the invention and 400 mg of sulfamethoxazole, a tablet for children can contain 20 mg of a compound I in accordance with the invention and 100 mg of sulfamethoxazole; syrup (per 5 ml) can contain 40 mg of compound I and 200 mg of sulfamethoxazole.

The compounds of formula I are characterized by a high antibacterial activity and, respectively, a pronounced synergistic effect in combination with sulfonamides and good tolerance.

The following Examples illustrate the invention.

Example 1 (Key Intermediate)

5-(4-Ethoxy-1H-indol-6-ylmethyl)-pyrimidine-2,4-diamine. This compound was produced from 4-hydroxy-1H-indole-6-carboxylic acid methyl ester (DE 2508251) via steps a)–f) as described below.

a) 4-Ethoxy-1 H-indole-6-carboxylic Acid Methyl Ester. Potassium tert-butylate (581 mg, 5.18 mmol) was added at 0° C. to a solution of 4-hydroxy-1-indole-6-carboxylic acid methyl ester (900 mg, 4.71 mmol) and iodoethane (0.81 g, 5.18 mmol) in N,N-dimethylformamide (10 mL). The reaction mixture was stirred 30 min at 0° C. and 90 min at room temperature, then poured onto ice and extracted with ethyl acetate. The organic layer was washed with brine, dried ($MgSO_4$), and evaporated. Column chromatography ($SiO_2$; n-hexane/ethyl acetate 3:1) afforded the title compound (275 mg, 22%). Yellow solid.

MS (EI): 219.1 ($M^+$)

b) (4-Ethoxy-1H-indol-6-yl)-methanol. Diisobutylaluminium hydride(1 M solution in tetrahydrofuran, 4.9 mL, 4.9 mmol) was added at 0° C. over 20 min to a solution of 4-ethoxy-1indole-6-carboxylic acid methyl ester (270 mg, 1.23 mmol) in tetrahydrofuran (10 mL). After 2.5 h the reaction was quenched through the addition of water (2 mL). Addition of brine (10 mL), saturated aqueous ammonium chloride solution (10 mL), ethyl acetate (20 mL), filtration through filter aid, separation of the organic layer, drying ($MgSO_4$) and evaporation yielded the title compound (218 mg, 89%). Light brown solid.

MS (EI): 191 ($M^+$)

c) 4-Ethoxy-1H-indole-6-carbaldehyde. A mixture of (4-ethoxy-1H-indol-6-yl)-methanol (180 mg, 0.941 mmol) and manganese dioxide (410 mg, 4.71 mmol) was refluxed in dichloromethane (10 mL) for 16 h. After filtration through filter aid and evaporation the title compound (147 mg, 78%) was obtained. Dark brown solid.

MS (EI): 189 ($M^+$)

d) 4-Ethoxy-1-(2-trimethylsilanyl-ethoxymethyl)-1H indole-6-carbaldehyde. Potassium tert-butylate (753 mg, 6.71 mmol) was added at 0° C. to a solution of 4-ethoxy-1H-indole-6-carbaldehyde (1.27 g, 6.71 mmol) in N,N-dimethylformamide (25 mL). 2-(trimethyl-silyl) ethoxymethyl chloride (1.23 g, 7.38 mmol) was added after 1 h, then after 2 h the mixture was treated with potassium tert-butylate (377 mg, 3.36 mmol) and 2-(trimethyl-silyl) ethoxymethyl chloride (616 mg, 3.69 mmol). The reaction mixture was allowed to warm to room temperature and stirred overnight, then poured onto ice and extracted with ethyl acetate. The organic layer was washed with brine, dried ($MgSO_4$), and evaporated. Flash chromatography ($SiO_2$; n-hexane/ethyl acetate 2:1) afforded the title compound (2.14 g, 100%). Yellow oil.

MS (EI): 319 ($M^+$)

e) 5-[4-Ethoxy-1-(2-trimethylsilanyl-ethoxymethyl)-1H-indol-6-ylmethyl]-pyrimidine-2,4-diamine. A warm solution of potassium tert-butylate (900 mg, 8.02 mmol) in tert-butanol (7.5 mL) was added at room temperature to a solution of 4-ethoxy-1-(2-trimethylsilanyl-ethoxymethyl)-1H-indole-6-carbaldehyde (2.14 g, 6.69 mmol) and 3-anilinopropionitrile (1.08 g, 7.36 mmol) in methyl sulfoxide (25 mL). After 90 min the solution was treated with water and the suspension formed was stirred for 2 h. The precipitate was collected by filtration and dried. This material was added to a suspension of guanidine hydrochloride (1.90 g, 19.9 mmol) and potassium tert-butylate (2.23 g, 19.9 mmol) in ethanol (100 mL), and the reaction mixture was refluxed for 16 h, then most of the solvent was distilled off, and ether (50 mL) was added. Insoluble material was removed by filtration, the filtrate was washed with water, dried ($MgSO_4$), and evaporated. The residue was washed with diethyl ether/n-hexane 4:3 (70 mL) to afford the title compound (1.71 g, 62%). Light brown solid.

MS (ISP): 414.4 ($[M+H]^+$)

f) 5-(4-Ethoxy-1H-indol-6-ylmethyl)-pyrimidine-2,4-diamine. A solution of 5-[4-ethoxy-1-(2-trimethylsilanyl-ethoxymethyl)-1H-indol-6-ylmethyl]-pyrimidine-2,4-diamine (1.20 g, 2.90 mmol), ethylenediamine (785 mg, 13.1 mmol) and tetrabutylammonium fluoride (1M solution in tetrahydrofuran, 8.7 mL, 8.7 mmol) was stirred 18 h at 80° C. in the presence of molecular sieves (4 Å). After separation of the sieves, the reaction mixture was poured onto ice and extracted with ethyl acetate. The organic layer was washed with brine, dried ($MgSO_4$), and evaporated. Flash chromatography ($SiO_2$; $CH_2Cl_2$/MeOH/$NH_4OH$ 90:10:1) afforded the title compound (610 mg, 74%).Yellow solid.

MS (ISP): 284.2 ($[M+H]^+$)

Example 2a 5-(1-cyclopropylmethyl-4-ethoxy-1H-indol-6-ylmethyl)-pyrimidine-2,4-diamine. Potassium tert-butylate (67 mg, 0.60 mmol) was added at room temperature to a solution of 5-(4-ethoxy-1H-indol-6-ylmethyl)-pyrimidine-2,4-diamine (Example 1; 141 mg, 0.50 mmol) in N,N-dimethylformamide (2 mL). After 30 min (bromomethyl) cyclopropane (87 mg, 0.65 mmol) was added, then after 1 h the reaction mixture was poured into ice water and extracted with ethyl acetate. The organic layer was dried ($MgSO_4$), and evaporated. Column chromatography ($SiO_2$; $CH_2Cl_2$/MeOH/$NH_4OH$ 19:1:0.05) afforded the title compound (65 mg, 38%). Off-white solid.

MS (ISP): 338.3 ($[M+H]_+$)

Example 2b 5-(1-Cyclopentyl-4-ethoxy-1H-indol-6-ylmethyl)-pyrimidine-2,4-diamine. This compound was produced by reaction of 5-(4-ethoxy-1H-indol-6-ylmethyl)-pyrimidine-2,4-diamine (Example 1; 100 mg, 0.353 mmol) with bromocyclopentane (334 mg, 2.24 mmol), following the procedure detailed in Example 2a. Yield: 66 mg (53%). Off-white solid.

MS (ISP): 352.3 ($[M+H]^+$)

Example 2c 5-(1-Benzyl-4-ethoxy-1H-indol-6-ylmethyl)-pyrimidine-2,4-diamine. This compound was produced by reaction of 5-(4-ethoxy-1H-indol-6-ylmethyl)-pyrimidine-2,4-diamine (Example 1; 100 mg, 0.353 mmol) with benzyl bromide (73 mg, 0.42 mmol), following the procedure detailed in Example 2a. Yield: 100 mg (76%). Off-white solid.

MS (ISP): 374.4 ([M+H]$^+$)

Example 2d

5-[4-Ethoxy-1-(propane-2-sulfonyl)-1H-indol-6-ylmethyl]-pyrimidine-2,4-diamine. Potassium tert-butylate (71 mg, 0.64 mmol) was added at room temperature to a solution of 5-(4-ethoxy-1H-indol-6-ylmethyl)-pyrimidine-2,4-diamine (Example 1; 150 mg), 0.53 mmol) in N,N-dimethylformamide (4 mL) containing molecular sieves (4 Å). After 20 min propane-2-sulfonyl chloride (91 mg, 0.64 mmol) was added, then after 90 min the reaction mixture was treated with potassium tert-butylate (24 mg, 0.21 mmol) and propane-2-sulfonyl chloride (31 mg, 0.21 mmol). After 90 min the reaction mixture was poured onto ice and extracted with ethyl acetate. The organic layer was dried (MgSO$_4$), and evaporated. Flash chromatography (SiO$_2$; CH$_2$Cl$_2$/MeOH/NH$_4$OH 19:1:0.05) afforded the title compound (109 mg, 53%). White solid.

MS (EI): 389 (M$^+$)

Example 2e 6-(2,4-Diamino-pyrimidin-5-ylmethyl)-4-ethoxy-indole-1-sulfonic Acid dimethylamide. Potassium tert-butylate (42 mg, 0.37 mmol) was added to a solution of 5-(4-ethoxy-1H-indol-6-ylmethyl)-pyrimidine-2,4-diamine (Example 1; 100 mg, 0.353 mmol) in N,N-dimethylformamide (5 mL). After 15 min dimethylsulfamoyl chloride (53 mg, 0.37 mmol) was added, then after 30 min the solvent was distilled off and the residue partitioned between ethyl acetate and saturated aqueous sodium hydrogencarbonate solution. The organic layer was washed with brine, dried (MgSO$_4$), and evaporated. Suspension of the residue in ether and collection of the precipitate afforded the title compound (73 mg, 53%). Off-white solid.

MS (ISP): 374.4 ([M+H]$^+$)

Example 3

5-(4-Ethoxy-1-ethyl-1H-indol-6-ylmethyl)-pyrimidine-2,4-diamine. This compound was produced from of 4-hydroxy-1H-indole-6-carboxylic acid methyl ester (DE 2508251) via steps a)–d) as described below.

a) 4-Ethoxy-1-ethyl-1H-indole-6-carboxylic acid methyl ester. Potassium tert-butylate (3.13 g, 27.9 mmol) was added over 30 min to a solution of 4-hydroxy-1H-indole-6-carboxylic acid methyl ester (4.85 g, 25.4 mmol) and bromoethane (3.04 g, 27.9 mmol) at 0° C. After 75 min the solvent was evaporated and the residue partitioned between ethyl acetate and water. The organic layer was dried (MgSO$_4$), and evaporated. Column chromatography (SiO$_2$; hexane/ethyl acetate 3:1) afforded the title compound (550 mg, 9%). Light yellow solid.

MS (EI): 247 (M$^+$)

b) (4-Ethoxy-1-ethyl-1H-indol-6-yl)-methanol. This compound was produced by reaction of 4-ethoxy-1-ethyl-1H-indole-6-carboxylic acid methyl ester (540 mg, 2.18 mmol) with diisobutylaluminum hydride (1 M solution in tetrahydrofuran, 6.5 mL, 6.5 mmol), following the procedure detailed in Example 1, step b. Yield: 457 mg (95%). Light yellow solid.

MS (EI): 219 (M$^+$)

c) 4-Ethoxy-1-ethyl-1H-indole-6-carbaldehyde. This compound was produced by reaction of (4-ethoxy-1-ethyl-1H-indol-6-yl)-methanol (431 mg, 1.97 mmol) with manganese dioxide (1.03 g, 11.7 mmol), following the procedure detailed in Example 1. step c. Yield: 364 mg (85%). Light yellow solid.

MS (EI): 217 (M$^+$)

d) 5-(4-Ethoxy-1-ethyl-1H-indol-6-ylmethyl)-pyrimidine-2,4-diamine. This compound was produced from 4-ethoxy-1-ethyl-1H-indole-6-carbaldehyde (316 mg, 1.46 mmol), 3-anilinopropionitrile (234 mg, 1.60 mmol), and guanidine hydrochloride (256 mg, 2.67 mmol), following the procedure detailed in Example 1, step f. Yield: 165 mg (36%). Light brown solid.

MS (ISP): 312.2 ([M+H]$^+$)

Example 4 (Key Intermediate)

6-(2,4-Diamino-pyrimidin-5-ylmethyl)-1-methyl-1H-indol-4-ol. This compound was produced from 4-acetyl-1H-indole-6-carboxylic acid methyl ester (J. Prakt. Chem. 1973, 315, 295–299) via steps a)-g) as described below.

a) 1-Acetyl-4-(2-trimethylsilanyl-ethoxymethoxy)-1H-indole-6-carboxylic acid methyl ester. Potassium tert-butylate (477 mg, 4.17 mmol) was added to a solution of 4-acetyl-1H-indole-6-carboxylic acid methyl (972 mg, 4.17 mmol) in N,N-dimethylformamide (15 mL) at 0° C. After 1 h 2-(trimethylsilyl)ethoxymethyl chloride (849 mg, 4.58 mmol) was added, then after 2 h the reaction mixture was poured onto ice and extracted with ethyl acetate. The organic layer was washed with water and brine, dried (MgSO$_4$), and evaporated to yield the title compound (1.40 g, 92%). Light brown solid.

MS (ISP): 364.4 ([M+H ]$^+$), 381.4 ([M+NH$_4$]$^+$)

b) 4-(2-Trimethylsilanyl-ethoxymethoxy)-1H-indole-6-carboxylic acid methyl ester. A suspension of 1-acetyl-4-(2-trimethylsilanyl-ethoxymethoxy)-1H-indole-6-carboxylic acid methyl ester (4.50 g, 12.4 mmol) in methanol (200 mL), water (50 mL), and saturated aqueous sodium hydrogen carbonate solution (50 mL) was stirred for 105 min at room temperature, then poured onto ice and extracted with ethyl acetate. The organic layer was washed with brine, dried (MgSO$_4$), and evaporated to afford the title compound (3.52 g, 91%). Brown oil.

MS (EI): 263 ([M—CH$_2$O—C$_2$H$_4$]$^+$),321 (M$^+$)

c) 1-Methyl-4-(2-trimethylsilanyl-ethoxymethoxy)-1H-indole-6-carboxylic acid methyl ester. Potassium tert-butylate (2.98 g, 26.0 mmol) was added to a solution of 4-(2-trimethylsilanyl-ethoxymethoxy)-1H-indole-6-carboxylic acid methyl ester (7.60 g, 23.6 mmol) in N,N-dimethylformamide (110 mL). After 45 min iodomethane (3.73 g, 26.0 mmol) was added, then after 45 min the reaction mixture was partitioned between saturated aqueous ammonium chloride solution and ethyl acetate. The organic layer was washed with saturated aqueous sodium hydrogencarbonate solution, water, and brine, dried (MgSO$_4$), and evaporated to afford the title compound (7.92 g, 100%). Red oil.

MS (EI): 277 ([M—CH$_2$O—C$_2$H$_4$]$^+$), 335 (M$^+$)

d) [1-Methyl-4-(2-trimethylsilanyl-ethoxymethoxy)-1H-indol-6-yl] -methanol. This compound was produced by reaction of 1-methyl-4-(2-trimethylsilanyl-ethoxymethoxy)-1H-indole-6-carboxylic acid methyl ester (7.98 g, 23.8 mmol) with diisobutylaluminum hydride (1 M solution in tetrahydrofuran, 96 mL, 96 mmol), following the procedure detailed in Example 1, step b. Yield: 6.32 g (86%). Red oil.

MS (ISP): 308.3 ([M+H]$^+$)

e) 1-Methyl-4-(2-trimethylsilanyl-ethoxymethoxy)-1H-indole-6-carbaldehyde. This compound was produced by reaction of [1-methyl-4-(2-trimethylsilanyl-ethoxymethoxy)-1H-indol-6-yl]-methanol (6.27 g, 20.4 mmol) with manganese dioxide (9.85 g, 102 mmol), following the procedure detailed in Example 1, step c. Yield: 6.06 g (97%). Yellow solid.

MS (EI): 247 ([M—$CH_2O$—$C_2H_4$]$^+$), 305 (M$^+$)

f) 5-[1-Methyl-4-(2-trimethylsilanyl-ethoxymethoxy)-1H-indol-6-ylmethyl]-pyrimidine-2,4-diamine. A warm solution of potassium tert-butylate (2.68 g, 23.4 mmol) in tert-butanol (20 mL) was added to a room temperature solution of 1-methyl-4-(2-trimethylsilanyl-ethoxymethoxy)-1H-indole-6-carbaldehyde (5.95 g, 19.5 mmol) and 3-anilinopropionitrile (3.20 g, 21.4 mmol) in methyl sulfoxide (70 mL). After 2 h the solution was diluted with ethyl acetate, washed with water and brine, dried ($MgSO_4$), and evaporated. This material was dissolved in ethanol (70 mL) and added to a suspension of guanidine hydrochloride (6.21 g, 64.4 mmol) in ethanol (210 mL), and the mixture was stirred at 70° C. for 22 h. Most of the solvent was distilled off, and the residue was partitioned between water and ether. The organic layer was washed with brine, dried ($MgSO_4$), and evaporated. Flash chromatography ($SiO_2$; $CH_2CL_2$/MeOH/$NH_4OH$ 19:1:0.05) afforded the title compound (3.32 g, 43%).Yellow solid.

MS (ISP): 400.4 ([M+H]$^+$)

g) 6-(2,4-Diamino-pyrimidin-5-ylmethyl)-1-methyl-1H-indol-4-ol. A solution of sulfuric acid (7.25 mL) in methanol (240 mL) was added at room temperature over 30 min to a solution of 5-[1-methyl-4-(2-trimethylsilanyl-ethoxymethoxy)-1H-indol-6-ylmethyl]-pyrimidine-2,4-diamine (3.22 g, 8.05 mmol) in methanol (240 mL) and tetrahydrofuran (240 mL). After 20 min the product was precipitated by addition of $NH_4OH$ (36 mL). The solvent was evaporated, the residue was suspended in water (160 mL), the pH was set to 9–10 with 25% aqueous ammonia solution and the mixture stirred for 45 min. The precipitate was filtered, washed with water, and dried to afford the title compound (2.17 g, 100%). Yellow solid.

MS (ISP): 270.4 ([M+H]$^+$)

Example 5a 5-(4-Cyclopropylmethoxy-1-methyl-1H-indol-6-ylmethyl)-pyrimidine-2,4-diamine. Potassium tert-butylate (82 mg, 0.72 mmol) was added at 0° C. to a solution of 6-(2,4-diamino-pyrimidin-5-ylmethyl)-1-methyl-1H-indol-4-ol (Example 4; 162 mg, 0.60 mmol) in N,N-dimethylformamide (16.5 mL). After 45 min the solution was treated with (bromomethyl)cyclopropane (100 mg, 0.72 mmol). The reaction mixture was allowed to warm to room temperature, stirred for 2.5 h, then poured into ice water, set to pH 9–10 with 25% aqueous ammonia solution, and extracted with ethyl acetate. The organic layer was washed with water and brine, dried ($MgSO_4$), and evaporated. Column chromatography ($SiO_2$; $CH_2Cl_2$/MeOH/$NH_4OH$ 19:1:0.05) afforded the title compound (127 mg, 65%). Yellow solid.

MS (ISP): 324.4 ([M+H]$^+$)

Example 5b 5-(4-Isopropoxy-1-methyl-1H-indol-6-ylmethyl)-pyrimidine-2,4-diamine. This compound was produced by reaction of 6-(2,4-diamino-pyrimidin-5-ylmethyl)-1-methyl-1H-indol-4-ol (Example 4; 293 mg, 1.09 mmol) with 2-bromopropane (162 mg, 1.31 mmol), following the procedure detailed in Example 5a. Yield: 132 mg (39%). Light orange solid.

MS (ISP): 312.2 ([M+H]$^+$)

Example 5c

Propane-2-sulfonic acid 6-(2,4-diamino-pyrimidin-5-ylmethyl)-1-methyl-1H-indol-4-yl ester. Potassium tert-butylate (150 mg, 1.31 mmol) was added at 0° C. (ice bath) to a solution of 6-(2,4-diamino-pyrimidin-5-ylmethyl)-1-methyl-1H-indol-4-ol (Example 4; 293 mg, 1.09 mmol) in N,N-dimethylformamide (33 mL). After 30 min the solution was treated with propane-2-sulfonyl chloride (190 mg, 1.31 mmol), and the ice bath was removed. After 2.5 h the reaction mixture was poured into ice water, set to pH 9–10 with 25% aqueous ammonia solution, and extracted with ethyl acetate. The organic layer was washed with water and brine, dried ($MgSO_4$), and evaporated. Column chromatography ($SiO_2$; $CH_2Cl_2$/MeOH/$NH_4OH$19:1:0.05) afforded the title compound (153 mg, 37%). White solid.

MS (ISP): 376.4 ([M+H]$^+$)

Example 5d

2-Methyl-propane-1-sulfonic acid 6-(2,4-diamino-pyrimidin-5-ylmethyl)-1-methyl-1H-indol-4-yl ester.

This compound was produced by reaction of 6-(2,4-diamino-pyrimidin-5-ylmethyl)-1-methyl-1H-indol-4-ol (Example 4,269 mg, 1.00 mmol) with 2-methylpropane-1-sulfonyl chloride (188 mg, 1.20 mmol), following the procedure detailed in Example 5c. Yield: 58 mg (15%). White solid.

MS (ISP): 390.3 ([M+H]$^+$)

Example 5e rac-Butane-2-sulfonic acid 6-(2,4-diamino-pyrimidin-5-ylmethyl)-1-methyl-1H-indol-4-yl ester. This compound was produced by reaction of 6-(2,4-diamino-pyrimidin-5-ylmethyl)-1-methyl-1H-indol-4-ol (Example 4; 294 mg, 1.09 mmol) with rac-butane-2-sulfonyl chloride (205 mg, 1.31 mmol), following the procedure detailed in Example 5c. Yield: 107 mg (25%). White solid.

MS (ISP): 390.3 ([M+H]$^+$)

Example 6 (Key Intermediate)

6-(2,4-Diamino-pyrimidin-5-ylmethyl)-1-ethyl-1H-indol-4-ol This compound was produced from 4-(2-trimethylsilanyl-ethoxymethoxy)-1H-indole-6-carboxylic acid methyl ester (Example 4. step b) via steps a)-e) as described below.

a) 1-Ethyl-4-(2-trimethylsilanyl-ethoxymethoxy)-1H-indole-6-carboxylic acid methyl ester. Potassium tert-butylate (3.92 g, 34.2 mmol) was added at room temperature to a solution of 4-(2-trimethylsilanyl-ethoxymethoxy)-1H-indole-6-carboxylic acid methyl ester (10.0 g, 31.1 mmol). After 45 min the solution was treated with bromoethane (3.77 g, 34.2 mmol), then after 45 min the solvent was evaporated and the residue partitioned between ethyl acetate and saturated aqueous ammonium chloride solution. The organic layer was washed with saturated aqueous sodium hydrogencarbonate solution, water, and brine, dried ($MgSO_4$), and evaporated to afford the title compound (10.1 g, 93%). Red solid.

MS (ISP): 350.3 ([M+H]$^+$)

b) [1-Ethyl-4-(2-trimethylsilanyl-ethoxymethoxy)-1H-indol-6-yl]-methanol. This compound was produced by reaction of 1-ethyl-4-(2-trimethylsilanyl-ethoxymethoxy)-1H-indole-6-carboxylic acid methyl ester (9.09 g, 2.60 mmol) with diisobutylaluminum hydride (1 M solution in tetrahydrofuran, 104 mL, 104 mmol), following the procedure detailed in Example 1, step b. Yield: 7.86 g (94%). Orange oil.

MS (EI): 263 ([M—CH$_2$O—C$_2$H$_4$]$^+$), 321 (M$^+$)

c) 1-Ethyl-4-(2-trimethylsilanyl-ethoxymethoxy)-1H-indole-6-carbaldehyde. This compound was produced by reaction of [1-ethyl-4-(2-trimethylsilanyl-ethoxymethoxy)-1H-indol-6-yl]-methanol (7.72 g, 2.40 mmol) with manganese dioxide (11.6 g, 120 mmol), following the procedure detailed in Example 1, step c. Yield: 7.49 g (98%). Yellow solid.

MS (EI): 261 ([M—CH$_2$O—C$_2$H$_4$]$^+$), 319 (M$^+$)

d) 5-[1-Ethyl-4-(2-trimethylsilanyl-ethoxymethoxy)-1H-indol-6-ylmethyl]-pyrimidine-2,4-diamine. This compound was produced from 1-ethyl-4-(2-trimethylsilanyl-ethoxymethoxy)-1H-indole-6-carbaldehyde (630 mg, 1.97 mmol), 2-anilinopropionitrile (324 mg, 2.17 mmol), and guanidine hydrochloride (634 mg, 6.60 mmol), following the procedure detailed in Example 4, step f. Yield: 425 mg (53%). Yellow solid.

MS (ISP): 414.4 ([M+H]$^+$)

e) 6-(2,4-Diamino-pyrimidin-5-ylmethyl)-1-ethyl-1H-indol-4-ol. Tetrabutylammonium fluoride (1 M solution in tetrahydrofuran, 33.4 mL, 33.4 mmol) and ethylenediamine (3.02 g, 50.1 mmol) were added at room temperature to a solution of 5-[1-ethyl-4-(2-trimethylsilanyl-ethoxymethoxy)-1H-indol-6-ylmethyl]-pyrimidine-2,4-diamine (4.60 g, 11.1 mmol) in N,N-dimethylformamide (50 mL) containing molecular sieves (4 Å). After heating this mixture to 80° C. for 3.5 h, the solvent was evaporated. The residue was dissolved in hot methanol (500 mL), SiO$_2$ (10 g) was added, the solvent was evaporated, and the residue was loaded on a column (90 g SiO$_2$) and chromatographed (CH$_2$Cl$_2$MeOH/NH$_4$OH 90:10:1), affording the crude product which was suspended in ether. Filtration of the precipitate yielded the title compound (1.04 g, 33%). Yellow solid.

MS (ISP): 284.2 ([M+H]$^+$)

Example 7a 5-(4-Cyclopropylmethoxy-1-ethyl-1H-indol-6-ylmethyl)-pyrimidine-2,4-diamine. This compound was produced by reaction of 6-(2,4-diamino-pyrimidin-5-ylmethyl)-1-ethyl-1H-indol-4-ol (Example 6; 94 mg, 0.33 mmol) with (bromomethyl)cyclopropane (55 mg, 0.40 mmol), following the procedure detailed in Example 5a. Yield: 50 mg (45%). Yellow solid.

MS (EI): 337 (M$^+$)

Example 7b 5-(1-Ethyl-4-methoxy-1H-indol-6-ylmethyl)-pyrimidine-2,4-diamine. This compound was produced by reaction of 6-(2,4-diamino-pyrimidin-5-ylmethyl)-1-ethyl-1H-indol-4-ol (Example 6; 196 mg, 0.69 mmol) with iodomethane (118 mg, 0.83 mmol), following the procedure detailed in Example 5a. Yield: 77 mg (37%). Orange solid.

MS (ISP): 298.3 ([M+H ]$^+$)

Example 7c 5-(1-Ethyl-4-isopropoxy-1H-indol-6-ylmethyl)-pyrimidine-2,4-diamine. This compound was produced by reaction of 6-(2,4-diamino-pyrimidin-5-ylmethyl)-1-ethyl-1H-indol-4-ol (Example 6; 292 mg, 1.03 mmol) with 2-bromopropane (153 mg, 1.23 mmol), following the procedure detailed in Example 5a. Yield: 89 mg (27%). Yellow solid.

MS (ISP): 326.4 ([M+H]$^+$)

Example 7d 5-(1-Ethyl-4-prop-2-ynyloxy-1H-indol-6-ylmethyl)-pyrimidine-2,4-diamine. This compound was produced by reaction of 6-(2,4-diamino-pyrimidin-5-ylmethyl)-1-ethyl-1H-indol-4-ol (Example 6; 141 mg, 0.498 mmol) with propargyl chloride (70% solution in toluene, 66 µl, 0.60 mmol), following the procedure detailed in Example 5a. Yield: 48 mg (30%). Brown solid.

MS (ISP): 322.3 ([M+H]$^+$)

Example 7e

5-[4-([1,3]Dioxolan-2-ylmethoxy)-1-ethyl-1H-indol-6-ylmethyl]-pyrimidine-2,4-diamine. This compound was produced by reaction of 6-(2,4-diamino-pyrimidin-5-ylmethyl)-1-ethyl-1H-indol-4-ol (Example 6; 57 mg, 0.20 mmol) with 2-bromomethyl-1,3-dioxolane (40 mg, 0.24 mmol), following the procedure detailed in Example 5a. Yield: 21 mg (28%). Yellow solid.

MS (ISP): 370.3 ([M+H]$^+$)

Example 7f 5-(4-Cyclobutylmethoxy-1-ethyl-1H-indol-6-ylmethyl)-pyrimidine-2,4-diamine. This compound was produced by reaction of 6-(2,4-diamino-pyrimidin-5-ylmethyl)-1-ethyl-1H-indol-4-ol (Example 6; 196 mg, 0.69 mmol) with (bromomethyl)cyclobutane (128 mg, 0.83 mmol), following the procedure detailed in Example 5a. Yield: 69 mg (28%). Orange solid.

MS (ISP): 352.3 ([M+H]$^+$)

Example 7g 5-(1-Ethyl-4-isobutoxy-1H-indol-6-ylmethyl)-pyrimidine-2,4-diamine. This compound was produced by reaction of 6-(2,4-diamino-pyrimidin-5-ylmethyl)-1-ethyl-1H-indol-4-ol (Example 6; 196 mg, 0.69 mmol) with 1-bromo-2-methylpropane (118 mg, 0.83 mmol), following the procedure detailed in Example 5a. Yield: 71 mg (30%). Yellow solid.

MS (EI): 339.2 (M$^+$)

Example 7h

5-[1-Ethyl-4-(1-methyl-cyclopropylmethoxy)-1H-indol-6-ylmethyl]-pyrimidine-2,4-diamine. This compound was produced by reaction of 6-(2,4-diamino-pyrimidin-5-ylmethyl)-1-ethyl-1H-indol-4-ol (Example 6; 196 mg, 0.69 mmol) with 1-bromomethyl-1-methylcyclopropane (124 mg, 0.83 mmol), following the procedure detailed in Example 5a. Yield: 167 mg (68%).Yellow solid.

MS (ISP): 352.4 ([M+H]$^+$)

Example 7i rac-5-[1-Ethyl-4-(tetrahydro-furan-2-ylmethoxy)-1H-indol-6-ylmethyl]-pyrimidine-2,4-diamine. This compound was produced by reaction of 6-(2,4-diamino-pyrimidin-5-ylmethyl)-1-ethyl-1H-indol-4-ol (Example 6; 198 mg, 0.70 mmol) with rac-tetrahydrofurfuryl bromide (193 mg, 1.05 mmol), following the procedure detailed in Example 5a. Yield: 65 mg (25%). Light brown solid.

MS (ISP): 368.3 ([M+H]$^+$)

Example 8a

Propane-2-sulfonic acid 6-(2,4-diamino-pyrimidin-5-ylmethyl)-1-ethyl-1H-indol-4-yl ester Propane-2-sulfonyl chloride (180 mg, 1.24 mmol) and potassium tert-butylate (142 mg, 1.24 mmol) were added at room temperature to a solution of 6-(2,4-diamino-pyrimidin-5-ylmethyl)-1-ethyl-1H-indol-4-ol (293 mg, 1.03 mmol)in N,N-dimethylformamide (30 mL). After 20 min the reaction mixture was poured into ice water and the pH was set to 9–10 with 25% aqueous ammonia solution. This mixture was stirred for 5 min and extracted with ethyl acetate. The organic layer was washed with water and brine, dried (MgSO$_4$), and evaporated. Flash chromatography (SiO$_2$; CH$_2$Cl$_2$/MeOH/NH$_4$OH 19:1:0.05) afforded the title compound (76 mg, 19%). Light yellow solid.

MS (ISP): 390.3 ([M+H]$^+$)

Example 8b

Cyclopropyl-methanesulfonic acid 6-(2,4-diamino-pyrimidin-5-ylmethyl)-1-ethyl-1H-indol-4-yl ester. This compound was produced by reaction of 6-(2,4-diamino-pyrimidin-5-ylmethyl)-1-ethyl-1H-indol-4-ol (Example 6; 196 mg, 0.690 mmol) with cyclopropylmethanesulfonyl chloride (95 mg, 0.83 mmol), following the procedure detailed in Example 8a. Yield: 113 mg (40%). Yellow solid.

MS (EI): 282.2 ([M—C$_4$H$_6$SO$_2$]$^+$), 401.1 (M$^+$)

$^1$H NMR (400 MHz, (CD$_3$)$_2$SO): 7.53 (s, 1H); 7.40 (d, J=3.2, 1H); 7.38 (s, 1H); 6.86(s, 1H); 6.45 (d, J=3.2, 1H); 6.09 (s, 2H); 5.67 (s, 2H); 4.17 (q, J=7.2, 2H); 3.72 (s, 2H); 3.52 (d, J=7.2, 2H); 1.35 (t, J=7.2, 3H); 1.25–1.15 (m, 1H); 0.70–0.65 (m, 2H); 0.45–0.40 (m, 2H).

Example 8c

2-Methyl-propane-1-sulfonic acid 6-(2,4-diamino-pyrimidin-5-ylmethyl)-1-ethyl-1H-indol-4-yl ester. This compound was produced by reaction of 6-(2,4-diamino-pyrimidin-5-ylmethyl)-1-ethyl-1H-indol-4-ol (Example 6; 196 mg, 0.690 mmol) with 2-methylpropane-1-sulfonyl chloride (218 mg, 1.39 mmol), following the procedure detailed in Example 8a. Yield: 68 mg (24%). Yellow solid.

MS (ISP): 404.5 ([M+H]$^+$)

$^1$H NMR (400 MHz, (CD$_3$)$_2$SO): 7.53 (s, 1H); 7.45–7.35 (m, 2H); 6.84 (s, 1H); 6.45 (d, J=2.8, 1H); 6.08 (s, 2H); 5.67 (s, 2H); 4.28 (q, J=7.2, 2H); 3.72 (s, 2H); 3.44 (d, J=6.8, 2H); 2.30–2.20 (m, 1H); 1.36 (q, J=7.2, 3H); 1.07 (d, J=6.4, 6H).

Example 8d rac-Butane-2-sulfonic acid 6-(2,4-diamino-pyrimidin-5-ylmethyl)-1-ethyl-1H-indol-4-yl ester. This compound was produced by reaction of 6-(2,4-diamino-pyrimidin-5-ylmethyl)-1-ethyl-1H-indol-4-ol (Example 6; 196 mg, 0.690 mmol) with rac-butane-2-sulfonyl chloride (131 mg, 0.83 mmol), following the procedure detailed in Example 8a. Yield: 81 mg (29%).Yellow solid.

MS (ISP): 404.5 ([M+H]$^+$)

$^1$H NMR (400 MHz, (CD$_3$)$_2$SO): 7.53 (s, 1H); 7.40 (d, J=2.8, 1H); 7.38 (s, 1H); 6.82 (s, 1H); 6.41 (d, J=2.8, 1H); 6.09 (s, 2H); 5.68 (s, 2H); 4.17 (q, J=7.2, 2H); 3.72 (s, 2H); 3.60–3.50 (m, 1H); 2.10–2.00 (m, 1H); 1.70–1.60 (m, 1H); 1.45 (d, J=6.8, 3H); 1.35 (t, J=7.2, 3H); 1.02 (t, J=7.2, 3H).

Example 9

Dimethyl-sulfamic Acid 6-(2,4-diamino-pyrimidin-5-ylmethyl)-1-ethyl-1H-indol-4-yl ester. Tetrabutylammonium bromide (61 mg, 0.19 mmol) and 50% aqueous sodium hydroxide solution (7.8 mL) were added to a suspension of 6-(2,4-diamino-pyrimidin-5-ylmethyl)-1-ethyl-1H-indol-4-ol (Example 6; 436 mg, 1.54 mmol) in dichloromethane (130 mL), and the mixture was vigorously stirred for 15 min. Dimethylsulfamoyl chloride (226 mg, 1.57 mmol) was added, then after 2 h another portion of dimethylsulfamoyl chloride (60 mg, 0.42 mmol) was added. After 16 h the reaction mixture was partitioned between dichloromethane (130 mL) and water (50 mL), the organic layer was washed with brine, dried (MgSO$_4$), and evaporated. The crude product was purified by preparative HPLC to afford the title compound (51 mg, 9%). Light brown solid.

MS (ISP): 391.3 ([M+H]$^+$)

Example 10a 5-(4-Cyclopropylmethoxy-1-ethyl-3-morpholin-4-ylmethyl-1H-indol-6-ylmethyl)-pyrimidine-2,4-diamine. Formaldehyde (35% aqueous solution, 41 µL, 0.48 mmol) was added at room temperature to a solution of morpholine (142 mg, 1.60 mmol) in acetic acid (1.6 mL) and water (0.2 mL). After 10 min 5-(4-cyclopropylmethoxy-1-ethyl-1H-indol-6-ylmethyl)-pyrimidine-2,4-diamine (Example 7a; 134 mg, 0.40 mmol) was added, then after 45 min the solution was concentrated. 1M aqueous sodium hydroxide solution (10 mL) was added to the viscous residue, then the suspension formed was stirred at room temperature for 1 h, the solvent was removed and the gummy precipitate washed with water and dried to afford the title compound (121 mg, 69%). Off-white solid.

MS (ISP): 350.4 ([M—C$_4$H$_8$NO]$^+$),437.5 ([M+H]$^+$)

Example 10b

Propane-2-sulfonic acid 6-(2,4-diamino-pyrimidin-5-ylmethyl)-1-ethyl-3-morpholino-4-ylmethyl-1H-indol-4-ester. This compound was produced from propane-2-sulfonic acid 6-(Example 8a; 2,4-diamino-pyrimidin-5-ylmethyl)-1-ethyl-1H-indol-4-yl ester (400 mg, 1.03 mmol), formaldehyde (35% aqueous solution, 106 µL, 1.23 mmol), and morpholine (358 mg, 4.11 mmol), following the procedure detailed in Example 10a. Yield: 353 mg (70%). Light yellow solid.

MS (ISP): 402.5 ([M—C$_4$H$_8$NO]$^+$), 489.4 ([M+H]$^+$)

Example 10c

Propane-2-sulfonic acid 6-(2,4-diamino-pyrimidin-5-ylmethyl)-1-ethyl-3-thiomorpholin-4-ylmethyl-1H-indol-4-yl ester. This compound was produced from propane-2-sulfonic acid 6-(2,4-diamino-pyrimidin-5-ylmethyl)-1-ethyl-1H-indol-4-yl ester (Example 8a; 105 mg, 0.27 mmol), thiomorpholine (114 mg, 1.08 mmol), and formaldehyde (35% aqueous solution, 28 µL, 0.32 mmol), following the procedure detailed in Example 10a. Yield: 108 mg (80%). White solid.

MS (ISP): 402.5 ([M—C$_4$H$_8$NS]$^+$), 505.3 ([M+H]$^+$)

Example 10d (cis/trans)-Propane-2-sulfonic acid 6-(2,4-diamino-pyrimidin-5-ylmethyl)-3-(2,6-dimethyl-morpholin-4-ylmethyl)-1-ethyl-1H-indol-4-yl ester. This compound was produced from propane-2-sulfonic acid 6-(2,4-diaminopyrimidin-5-ylmethyl)-1-ethyl-1H-indol-4-yl ester (Example 8a; 105 mg, 0.27 mmol), (cis/trans)-2,6-dimethylmorpholine (128 mg, 1.08 mmol), and formaldehyde (35% aqueous solution, 28 µL, 0.32 mmol), following the procedure detailed in Example 10a. Yield: 97 mg (69%). Off-white solid.

MS (ISP): 402.5 ([M—$C_6H_{10}NO]^+$), 517.3 ([M+H]$^+$)

Example 10e

Cyclopropyl-methanesulfonic acid 6-(2,4-diamino-pyrimidin-5-ylmethyl)-1-ethyl-3-morpholin-4-ylmethyl-1H-indol-4-yl ester. This compound was produced from cyclopropyl-methanesulfonic acid 6-(2,4-diamino-pyrimidin-5-ylmethyl)-1-ethyl-1H-indol-4-yl ester (Example 8b; 129 mg, 0.32 mmol), morpholine (114 mg, 1.28 mmol), and formaldehyde (35% aqueous solution, 33 µL, 0.38 mmol), following the procedure detailed in Example 10a. Yield: 138 mg (86%). Light yellow solid.

MS (ISP): 414.3 ([M—$C_4H_8NO]^+$), 517.3 ([M+H]$^+$)

Example 11

Propane-2-sulfonic acid 6-(2,4-diamino-pyrimidin-5-ylmethyl)-1-ethyl-3-formyl-1H-indol-4-yl ester. Phosphorus oxychloride (133 mg, 0.867 mmol) was added over 20 min to N,N-dimethylformamide (0.95 mL) at -5° C. Propane-2-sulfonic acid 6-(2,4-diamino-pyrimidin-5-ylmethyl)-1-ethyl-1H-4-yl ester (Example 8a; 277 mg, 0.710 mmol) was then added at +2° C. and the reaction mixture was stirred at 40° C. for 5.5 h. After evaporation of the solvent and addition of saturated aqueous sodium carbonate solution (15 mL) and ethanol (1 mL) the resulting mixture was stirred 2 h at room temperature. Extraction with ethyl acetate, washing of the organic layer with water and brine, drying (MgSO$_4$), evaporation, and purification by preparative HPLC afforded the title compound (32 mg, 11%). White solid.

MS (ISP): 418.3 ([M+H]$^+$)

Example 12a

Propane-2-sulfonic acid 6-(2,4-diamino-pyrimidin-5-ylmethyl)-1-ethyl-3-methyl-1H-indol-4-yl ester. Propane-2-sulfonic acid 6-(2,4-diamino-pyrimidin-5-ylmethyl)-1-ethyl-3-morpholin-4-ylmethyl-1H-indol-4-yl ester (Example 10d; 270 mg, 0.55 mmol) was dissolved in methanol (50 mL) and 1 M aqueous hydrochloric acid solution (0.6 mL) and hydrogenated at room temperature and atmospheric pressure for 16 h in the presence of palladium on activated charcoal (10%, 170 mg). The catalyst was removed by filtration through filter aid and the filtrate was concentrated. The residue was dissolved in water (10 mL) and the pH set to ≈9 with 25% aqueous ammonia solution. The precipitate was collected by filtration and purified by preparative HPLC to afford the title compound (63 mg, 28%). Off-white solid.

MS (ISP): 404.5 ([M+H ]$^+$)

Example 12b

Cyclopropyl-methanesulfonic acid 6-(2,4-diamino-pyrimidin-5-ylmethyl)-1-ethyl-3-methyl-1H-indol-4-yl ester. This compound was produced from cyclopropyl-methanesulfonic acid 6-(2,4-diamino-pyrimidin-5-ylmethyl)-1-ethyl-3-morpholin-4-ylmethyl-1H-indol-4-yl ester (Example 10e; 250 mg, 0.50 mmol), following the procedure detailed in Example 12a. Yield: 164 mg (75%). Off-white solid.

MS (EI): 416.4 (M$^+$)

$^1$H NMR (400 MHz, (CD$_3$)$_2$SO): 7.51 (s, 1H); 7.29 (s, 1H); 7.12 (s, 1H); 6.82 (s, 1H); 6.18 (s, 2H); 5.76 (s, 2H); 4.10 (q, J=7.2, 2H); 3.70 (s, 2H); 3.53 (d, J=7.2, 2H); 2.34 (s, 3H); 1.31 (t, J=7.2, 3H); 1.25–1.15 (m, 1H); 0.70–0.65 (m, 2H); 0.45–0.40 (m, 2H).

Example 13

5-(3-Bromo-4-cyclopropylmethoxy-1-ethyl-1H-indol-6-ylmethyl)-pyrimidine-2,4-diamine. This compound was produced from 6-(2,4-diamino-pyrimidin-5-ylmethyl)-1-ethyl-1H-indol-4-ol (Example 6) via steps a)-b) as described below.

a) 3-Bromo-6-(2,4-diamino-pyrimidin-5-ylmethyl)-1-ethyl-1H-indol-4-ol.

A solution of bromine (192 mg, 1.20 mmol) in N,N-dimethylformamide (4 mL) was added at room temperature to a solution of 6-(2,4-Diamino-pyrimidin-5-ylmethyl)-1-ethyl-1H-indol-4-ol (283 mg, 1.00 mmol) over 45 min. After 1 h the mixture was poured into ice-cold 0.5% aqueous ammonia solution containing 0.1% sodium metabisulfite (200 mL) and extracted with ethyl acetate. The organic layer was washed with brine, dried (MgSO$_4$), and evaporated. Addition of methanol to the gummy residue yielded a precipitate which was collected by filtration and dried to afford the title compound (90 mg, 25%). Off-white solid.

MS (ISP): 362.1/364.1 ([M+H]$^+$)

b) 5-(3-Bromo-4-cyclopropylmethoxy-1-ethyl-1H-indol-6-ylmethyl)-pyrimidine-2,4-diamine. This compound was produced by reaction of 3-bromo-6-(2,4-diamino-pyrimidin-5-ylmethyl)-1-ethyl-1H-indol-4-ol (77 mg, 0.21 mmol) with (bromomethyl)-cyclopropane (34 mg, 0.26 mmol), following the procedure detailed in Example 5a. Yield: 34 mg (38%). Light brown solid.

MS (ISP): 416.4/418.4 ([M+H]$^+$)

Example 14 (Key Intermediate)

6-(2,4-Diamino-pyrimidin-5-ylmethyl)-1-ethyl-2-methyl-1H-indol-4-ol. This compound was produced from (4-benzyloxy-1H-indol-6-yl)-methanol (DE 2508251) via steps a)–i) as described below.

a) rac-4-Benzyloxy-6-(tetrahydro-pyran-2-yloxymethyl)-1H-indole. A solution of (4-benzyloxy-1H-indol-6-yl)-methanol (19.1 g, 75.3 mmol), 3,4-dihydro-2H-pyran (19.0 g, 226 mmol), and pyridinium toluene-4-sulfonate (1.89 g, 7.53 mmol) in dichloromethane (150 mL) and tetrahydrofuran (150 mL) was stirred for 1 h at room temperature. The solution was then diluted with ethyl acetate, washed with water and brine, dried (MgSO$_4$), and evaporated. Flash chromatography (SiO$_2$; n-hexane/ethyl acetate/NH$_4$OH 75:25:0.1) afforded the title compound (21.4 g, 84%). White solid.

MS (EI): 337.2 (M$^+$)

b) rac-1-Benzenesulfonyl-4-benzyloxy-6-(tetrahydro-pyran-2-yloxymethyl)-1H-indole. rac-4-Benzyloxy-6-(tetrahydro-pyran-2-yloxymethyl)-1H-indole (21.4 g, 63.3 mmol) and tetrabutylammonium hydrogensulfate (32.2 g, 95.0 mmol) were heated in toluene (150 mL) until dissolved. After addition of 2 M aqueous sodium hydroxide solution (40 mL), a solution of benzenesulfonyl chloride (16.8 g, 95.0 mmol) in toluene (90 mL) was added over 5 min at room temperature. After 45 min the two-phase mixture was then poured into ice and extracted with ethyl acetate. The organic layer was washed with brine, dried (MgSO$_4$), and evaporated. Flash chromatography (SiO$_2$; n-hexane/ethyl acetate/NH$_4$OH 85:15:0.1) afforded the title compound (28.4 g, 94%). Colourless gum.

MS (EI): 477.1 (M$^+$)

c) rac-1-Benzenesulfonyl-4-benzyloxy-2-methyl-6-(tetrahydro-pyran-2-yloxymethyl)-1H-indole. A solution of rac-1-benzenesulfonyl-4-benzyloxy-6-(tetrahydro-pyran-2-yloxymethyl)-1H-indole (28.4 g, 59.5 mmol) in tetrahydrofuran (150 mL) was cooled to −30° C. and treated with tert-butyllithium (1.5 M solution in n-pentane, 79.3 mL, 119 mmol). The solution was allowed to warm to room temperature, then cooled to −30° C. and treated with a solution of iodomethane (21.1 g, 149 mmol) in tetrahydrofuran (100 mL). The resulting solution was allowed to reach room temperature, then poured into saturated aqueous ammonium chloride solution and extracted with ethyl acetate. The organic layer was washed with brine, dried (MgSO$_4$), and evaporated. Flash chromatography (SiO$_2$; n-hexane/ethyl acetate/NH$_4$OH 80:20:0.1) followed by recrystallisation in methanol afforded the title compound (13.4 g, 46%). White solid.

MS (EI): 491.1 (M$^+$)

d) (1-Benzenesulfonyl-4-benzyloxy-2-methyl-1H-indol-6-yl)-methanol. A mixture of rac-1-benzenesulfonyl-4-benzyloxy-2-methyl-6-(tetrahydro-pyran-2-yloxymethyl)-1H-indole (10.1 g, 20.6 mmol) and pyridinium toluene-4-sulfonate (518 mg, 2.06 mmol) in ethanol (500 mL) was stirred at 60° C. for 3 h. Evaporation of the solvent followed by flash chromatography (SiO$_2$; n-hexane/ethyl acetate/NH$_4$OH 70:30:0.1) afforded the title compound (7.55 g, 90%). White solid.

MS (ISP): 408.3 ([M+H]$^+$)

e) 1-Benzenesulfonyl-4-benzyloxy-2-methyl-1H-indole-6-carbaldehyde. This compound was produced by reaction of (1-benzenesulfonyl-4-benzyloxy-2-methyl-1H-indol-6-yl)-methanol (7.50 g, 18.4 mmol) with manganese dioxide (17.8 g, 184 mmol), following the procedure detailed in Example 1, step c. Yield: 7.25 g (97%). White solid.

MS (EI): 405.0 (M$^+$)

f) 4-Benzyloxy-2-methyl-1H-indole-6-carbaldehyde. 1-Benzenesulfonyl-4-benzyloxy-2-methyl-1H-indole-6-carbaldehyde (7.45 g, 18.3 mmol) was heated in methanol (550 mL) and tetrahydrofuran (150 mL) until dissolved. After addition of 2 M aqueous potassium hydroxide solution (186 mL) the suspension formed was stirred at 70° C. for 1 h. Evaporation of the solvent yielded a residue, which was partitioned between ether and water. The organic layer was washed with brine, dried (MgSO$_4$), and evaporated to afford the title compound (4.87 g, 100%). Light yellow solid.

MS (EI): 265.1 (M$^+$)

g) 4-Benzyloxy-1-ethyl-2-methyl-1H-indole-6-carbaldehyde. This compound was produced by reaction of 4-benzyloxy-2-methyl-1H-indole-6-carbaldehyde (4.87 g, 18.4 mmol) with bromoethane (6.00 g, 55.1 mmol), following the procedure detailed in Example 6. step a. Yield: 4.45 g (83%).Yellow solid.

MS (ISP): 294.3 ([M+H]$^+$)

h) 5-(4-Benzyloxy-1-ethyl-2-methyl-1H-indol-6-ylmethyl)-pyrimidine-2,4-diamine. This compound was produced from 4-benzyloxy-1-ethyl-2-methyl-1H-indol-6-carbaldehyde (2.50 g, 8.52 mmol), 3-anilinopropionitrile (1.18 g, 8.10 mmol), and guanidine hydrochloride (2.69 g, 28.1 mmol), following the procedure detailed in Example 4, step f. Yield: 1.66 g (50%). Yellow solid.

MS (ISP): 388.2 ([M+H]$^+$)

i) 6-(2,4-Diamino-pyrimidin-5-ylmethyl)-1-ethyl-2-methyl-1H-indol-4-ol. A mixture of 5-(4-Benzyloxy-1-ethyl-2-methyl-1H-indol-6-ylmethyl)-pyrimidine-2,4-diamine (1.55 g, 4.00 mmol) and palladium on activated charcoal (10%, 77.5 mg) in methanol (75 mL) and tetrahydrofuran (30 mL) was hydrogenated at atmospheric pressure and room temperature for 1 h. The suspension was passed through filter aid and the latter washed thoroughly with hot N,N-dimethylformamide. Evaporation of the filtrate and flash chromatography (SiO$_2$; CH$_2$Cl$_2$:MeOH:NH$_4$OH 90:10:0.25) afforded the title compound (1.08 g, 91%). Orange solid.

MS (ISP): 298.3 ([M+H]$^+$)

Example 15a 5-(4-Ethoxy-1-ethyl-2-methyl-1H-indol-6-ylmethyl)-pyrimidine-2,4-diamine. This compound was produced by reaction of 6-(2,4-diamino-pyrimidin-5-ylmethyl)-1-ethyl-2-methyl-1H-indol-4-ol (Example 14; 83 mg, 0.28 mmol) with bromoethane (32 mg, 0.29 mmol), following the procedure detailed in Example 5a. Yield: 89 mg (98%). Brown solid.

MS (ISP): 326.4 ([M+H]$^+$)

Example 15b 5-(4-Cyclopropylmethoxy-1-ethyl-2-methyl-1H-indol-6-ylmethyl)-pyrimidine-2,4-diamine. This compound was produced from 6-(2,4-diamino-pyrimidin-5-ylmethyl)-1ethyl-2-methyl-1H-indol-4-ol (Example 14; 800 mg, 1.69 mmol) and (bromomethyl)-cyclopropane (381 mg, 2.82 mmol), following the procedure detailed in Example 5a. Yield: 67 mg (72%). Light brown solid.

MS (ISP): 352.4 ([M+H]$^+$)

Example 15c rac-Butane-2-sulfonic acid 6-(2,4-diamino-pyrimidin-5-ylmethyl)-1-ethyl-2-methyl-1H-indol-4-yl ester. This compound was produced by reaction of 6-(2,4-diamino-pyrimidin-5-ylmethyl)-1-ethyl-2-methyl-1H-indol-4-ol (Example 14; 250 mg, 0.841 mmol) with rac-butane-2-sulfonyl chloride (184 mg, 1.18 mmol), following the procedure detailed in Example 8a. Yield: 70 mg (20%). Orange foam.

MS (ISP): 418.3 ([M+H]$^+$)

$^1$H NMR (250 MHz, (CD$_3$)$_2$SO): 7.50 (s, 1H); 7.30 (s, 1H); 6.77 (s, 1H); 6.20 (s, 1H); 6.09 (s, 2H); 5.69 (s, 2H); 4.12 (q, J=7.2, 2H); 3.70 (s, 2H); 3.60–3.45 (m, 1H); 2.40 (s, 3H); 2.15–2.00 (m, 1H); 1.75–1.60 (m, 1H); 1.44 (d, J=6.8, 3H); 1.24 (d, J=7.2, 3H); 1.02 (d, J=7.2, 3H).

Example 16 (Key Intermediate)

6-(2,4-Diamino-pyrimidin-5-ylmethyl)-1-ethyl-3-(3-methoxy-phenyl)-1H-indol-4-ol This compound was produced from 4-benzyloxy-1H-indole-6-carboxylic acid methyl ester (DE 2508251) via steps a)-g) as described below.

a) 4-Benzyloxy-1-ethyl-1H-indole-6-carboxylic acid methyl ester. This compound was produced by reaction of 4-benzyloxy-1H-indole-6-carboxylic acid methyl ester (43.9 g, 156 mmol) with bromoethane (19.3 g, 172 mmol), following the procedure detailed in Example 6, step a. Yield: 48.2 g (100%). Brown solid.

MS (EI): 309.2 (M+)

b) 4-Benzyloxy-3-bromo-1-ethyl-1H-indole-6-carboxylic acid methyl ester. A solution of bromine (1.55 g, 9.70 mmol) in N,N-dimethylformamide (5 mL) was added at room temperature over 3 min to a solution of 4-benzyloxy-1-ethyl-1H-indole-6-carboxylic acid methyl ester (3.00 g, 9.70 mmol) in N,N-dimethylformamide (85 mL). After 16 h the reaction mixture was poured into a 0.5% aqueous ammonia solution containing 0.1% sodium metabisulfite (600 mL) and extracted with ethyl acetate. The organic layer was washed with brine, dried ($MgSO_4$), and evaporated. Column chromatography ($SiO_2$; n-hexane/ethyl acetate 5:1) yielded the crude product which was washed with n-hexane to afford the title compound (1.95 g, 52%). White solid.

MS (EI): 387.0/389.0 (M+)

c) 4-Benzyloxy-1-ethyl-3-(3-methoxy-phenyl)-1H-indole-6-carboxylic acid methyl ester. 4-Benzyloxy-3-bromo-1-ethyl-1H-indole-6-carboxylic acid methyl ester (1.88 g, 4.85 mmol) and a solution of 3-methoxybenzene boronic acid (1.14 g, 7.28 mmol) in ethanol were added at room temperature to a suspension of tetrakis(triphenylphosphine)-palladium (280 mg, 0.242 mmol) in 1,2-dimethoxyethane (3 mL). After 10 min 2 M aqueous sodium carbonate solution (20.6 mL) was added and the mixture stirred at 90° C. for 1 h. The organic solvent was then evaporated and the mixture obtained partitioned between water and dichloromethane. The organic layer was washed with brine, dried ($MgSO_4$), and evaporated. Column chromatography ($SiO_2$; hexane/ethyl acetate 5:1) afforded the title compound (1.37 g, 68%). Yellow gum.

MS (ISP): 416.3 ([M+H]+)

d) [4-Benzyloxy-1-ethyl-3-(3-methoxy-phenyl)-1H-indol-6-yl]-methanol. This compound was produced by reaction of 4-benzyloxy-1-ethyl-3-(3-methoxy-phenyl)-1H-indole-6-carboxylic acid methyl ester (1.32 g, 3.17 mmol) with diisobutylaluminum hydride (1 M solution in tetrahydrofuran, 13 mL, 13 mmol), following the procedure detailed in Example 1. step b. Yield: 1.17 g (95%).

MS (EI): 387.1 (M+)

e) 4-Benzyloxy-1-ethyl-3-(3-methoxy-phenyl)-1H-indole-6-carbaldehyde. This compound was produced by reaction of [4-benzyloxy-1-ethyl-3-(3-methoxy-phenyl)-1H-indol-6-yl]-methanol (1.10 g, 2.84 mmol) with manganese dioxide (1.23 g, 14.2 mmol), following the procedure detailed in Example 1, step c. Yield: 1.09 g (100%). Brown oil.

MS (EI): 385.1 (M+)

f) 5-[4-Benzyloxy-1-ethyl-3-(3-methoxy-phenyl)-1H-indol-6-ylmethyl]-pyrimidine-2,4-diamine. This compound was produced from 4-benzyloxy-1-ethyl-3-(3-methoxy-phenyl)-1H-indole-6-carbaldehyde (940 mg, 2.44 mmol), 3-anilinopropionitrile (392 mg, 2.68 mmol), and guanidine hydrochloride (859 mg, 8.99 mmol), following the procedure detailed in Example 1, step e. Yield: 711 mg (61%). Light brown solid.

MS (ISP): 480.4 ([M +H]+)

g) 6-(2,4-Diamino-pyrimidin-5-ylmethyl)-1-ethyl-3-(3-methoxy-phenyl)-1H-indol-4-ol. This compound was produced by hydrogenation of 5-[4-benzyloxy-1-ethyl-3-(3-methoxy-phenyl)-1H-indol-6-ylmethyl]-pyrimidine-2,4-diamine (650 mg, 1.36 mmol), following the procedure detailed in Example 14, step i. Yield: 505 mg (93%). Off-white solid.

MS (ISP): 390.3 ([M+H]+)

Example 17a

5-[4-Ethoxy-1-ethyl-3-(3-methoxy-phenyl)-1H-indol-6-ylmethyl]-pyrimidine-2,4-diamine. This compound was produced by reaction of 6-(2,4-diamino-pyrimidin-5-ylmethyl)-1-ethyl-3-(3-methoxy-phenyl)-1-H-indol-4-ol (Example 16; 150 mg, 0.39 mmol) with iodoethane (66 mg, 0.42 mmol), following the procedure detailed in Example 5a. Yield: 42 mg (26%). Brown solid.

MS (ISP): 418.3 ([M+H]+)

Example 17b

5-[1-Ethyl-4-methoxy-3-(3-methoxy-phenyl)-1H-indol-6-ylmethyl]-pyrimidine-2,4-diamine. This compound was produced by reaction of 6-(2,4-diamino-pyrimidin-5-ylmethyl)-1-ethyl-3-(3-methoxy-phenyl)-1H-indol-4-ol (Example 16; 100 mg, 0.26 mmol) with iodomethane (44 mg, 0.31 mmol), following the procedure detailed in Example 5a. Yield: 35 mg (34%). Brown solid.

MS (ISP): 404.5 ([M+H]+)

Example A

| Tablets: | |
|---|---|
| Sulfamethoxazole | 400 mg |
| Compound of formula I, e.g., cyclopropyl-methanesulfonic acid 6-(2,4-diamino-pyrimidine-5-ylmethyl)-1-ethyl-1H-indol-4-yl ester | 80 mg |
| PRIMOJEL (starch derivative) | 6 mg |
| POVIDONE K30 (polyvinylpyrrolidone) | 8 mg |
| Magnesiumstearate | 6 mg |
| Total weight | 500 mg |

Example B

| Tablets: | |
|---|---|
| Compound of formula I, e.g., 2-methyl-propane-1-sulfonic acid 6-(2,4-diamino-pyrimidine-5-ylmethyl)-1-ethyl-1H-indol-4-yl ester | 100 mg |
| Corn starch | 15 mg |
| Talc | 3 mg |
| Magnesiumstearate | 2 mg |
| Total weight | 120 mg |

Example C

| Injection solutions: | |
|---|---|
| Compound of formula I, e.g., rac-butane-2-sulfonic acid 6-(2,4-diamino-pyrimidine-5-ylmethyl)-1-ethyl-1H-indol-4-yl ester | 5 mg |
| Glycofurol 75 | 0.2 ml |
| Aq. bidist. sterile | ad 1.0 ml |

Example D

| Injection solutions: | |
|---|---|
| Compound of formula I, e.g., rac-butane-2-sulfonic acid 6-(2,4-diamino-pyrimidine-5-ylmethyl)-1-ethyl-1H-indol-4-yl ester | 5 mg |
| Propylene glycol | 0.5 ml |
| Aq. bidist. sterile | ad 1.0 ml |

What is claimed is:

1. A compound having the formula (I):

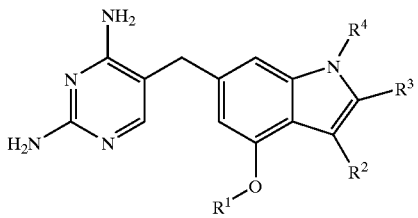

(I)

wherein
  $R^1$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl, or phenylalkyl;
  $R^2$ is hydrogen, halogen, alkyl, alkanoyl, phenyl, phenylalkyl or heterocyclylalkyl;
  $R^3$ is hydrogen or alkyl; and
  $R^4$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl, or phenylalkyl;
or pharmaceutically acceptable salts thereof.

2. The compound of claim 1, wherein $R^1$ is alkylsulfonyl, cycloalkylsulfonyl or cycloalkylalkylsulfonyl.

3. The compound of claim 2, wherein $R^1$ is isopropylsulfonyl, isobutylsulfonyl, sec-butylsulfonyl, cyclopropylsulfonyl or cyclopropylmethylsulfonyl.

4. The compound of claim 1, wherein $R^2$ is hydrogen or alkyl.

5. The compound of claim 4, wherein $R^2$ is methyl.

6. The compound of claim 1, wherein $R^3$ is hydrogen or methyl.

7. The compound of claim 1, wherein $R^4$ is alkyl.

8. The compound of claim 7, wherein $R^4$ is ethyl.

9. The compound of claim 1, wherein said compound is selected from the group consisting of
  cyclopropyl-methanesulfonic acid 6-(2,4-diamino-pyrimidin-5-ylmethyl)-1-ethyl-1H-indol-4-yl ester;
  2-methyl-propane-1-sulfonic acid 6-(2,4-diamino-pyrimidin-5-ylmethyl)-1-ethyl-1H-indol-4-yl ester;
  rac-butane-2-sulfonic acid 6-(2,4-diamino-pyrimidin-5-ylmethyl)-1-ethyl-1H-indol-4-yl ester;
  cyclopropyl-methanesulfonic acid 6-(2,4-diamino-pyrimidin-5-ylmethyl)-1-ethyl-3-methyl-1H-indol-4-yl ester; and
  rac-butane-2-sulfonic acid 6-(2,4-diamino-pyrimidin-5-ylmethyl)-1-ethyl-2-methyl-1H-indol-4-yl ester.

10. The compound of claim 1, wherein at least one of $R^2$ and $R^3$ is hydrogen.

11. A method for making a compound of formula (I) according to claim 1, comprising:

reacting a compound of the formula (II):

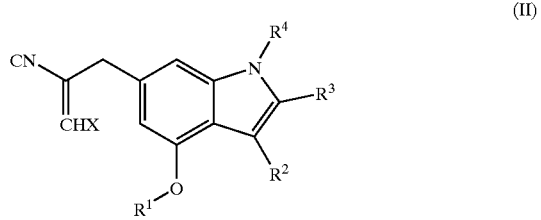

(II)

wherein $R^1$, $R^2$, $R^3$, and $R^4$ are as defined in claim 1 and X is a leaving group, with a guanindine or a salt thereof to make the compound of formula (I) of claim 1.

12. A method for making a compound of formula (I) of claim 1, comprising:
  introducing at least one of group $R^1$, $R^2$ and $R^4$ in a compound of formula (III)

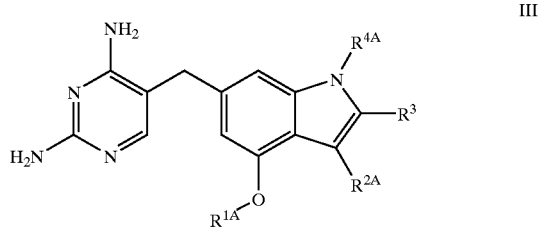

III wherein $R^3$ is as defined in claim 1, and $R^{1A}$, $R^{2A}$ and $R^{4A}$ are hydrogen or $R^1$, $R^2$ and $R^4$ respectively as defined in claim 1, provided that at least one of $R^{1A}$, $R^{2A}$ and $R^{4A}$ is a hydrogen atom.

13. A pharmaceutical composition comprising a pharmaceutically effective amount of a compound of formula (I):

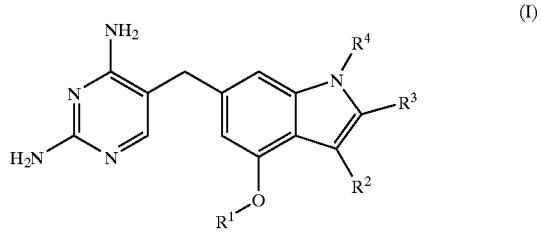

(I)

wherein
  $R^1$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl, or phenylalkyl;
  $R^2$ is hydrogen, halogen, alkyl, alkanoyl, phenyl, phenylalkyl heterocyclylalkyl;
  $R^3$ is hydrogen or alkyl; and
  $R^4$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl, or phenylalkyl;
or pharmaceutically acceptable salts thereof; and
a pharmaceutically acceptable carrier.

14. A method of treating an infection due to *Staphylococcus aureus* and *Streptococcus pneumoniae* comprising administering to a patient in need of such treatment, an effective amount of a compound of the formula (I):

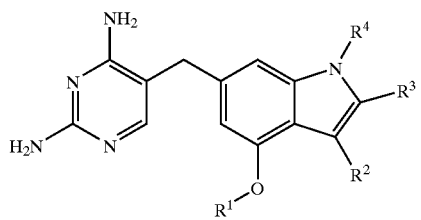

(I)

wherein $R^1$ is alkyl, alkenyl, alkynyl, cycloalkyl, cycloalkylalkyl, alkylsulfonyl, cycloalkylsulfonyl, cycloalkyl-alkylsulfonyl, dialkylsulfamoyl, N-cycloalkyl-N-alkylsulfamoyl, heterocyclylalkyl, or phenylalkyl;

$R^2$ is hydrogen, halogen, alkyl, alkanoyl, phenyl, phenylalkyl or heterocyclylalkyl;

$R^3$ is hydrogen or alkyl; and $R^4$ is alkyl, alkenyl, alkynyl, cycloalkyl, cycloalkylalkyl, alkylsulfonyl, cycloalkylsulfonyl, cycloalkylalkylsulfonyl, dialkylsulfamoyl, N-cycloalkyl-N-alkylsulfamoyl, heterocyclylalkyl, or phenylalkyl;

or pharmaceutically acceptable salts thereof.

* * * * *